US008799013B2

(12) United States Patent (10) Patent No.: US 8,799,013 B2
Gustafson (45) Date of Patent: Aug. 5, 2014

(54) MAMMOGRAPHY INFORMATION SYSTEM

(75) Inventor: Gregory A. Gustafson, Maple Plain, MN (US)

(73) Assignee: PenRad Technologies, Inc., Buffalo, MN (US)

( * ) Notice: Subject to any disclaimer, the term of this patent is extended or adjusted under 35 U.S.C. 154(b) by 801 days.

(21) Appl. No.: 12/953,100

(22) Filed: Nov. 23, 2010

(65) Prior Publication Data
US 2011/0137132 A1 Jun. 9, 2011

Related U.S. Application Data

(63) Continuation-in-part of application No. 12/625,898, filed on Nov. 25, 2009.

(60) Provisional application No. 61/282,000, filed on Nov. 24, 2009.

(51) Int. Cl.
| | |
|---|---|
| *G06Q 10/00* | (2012.01) |
| *G06Q 50/00* | (2012.01) |
| *A61B 5/00* | (2006.01) |
| *G06F 19/00* | (2011.01) |
| *A61B 5/08* | (2006.01) |
| *A61B 5/06* | (2006.01) |

(52) U.S. Cl.
CPC ............. *A61B 5/4312* (2013.01); *A61B 5/7264* (2013.01); *A61B 5/08* (2013.01); *G06F 19/3443* (2013.01); *A61B 5/06* (2013.01); *G06F 19/321* (2013.01)
USPC .................................... 705/2; 705/3; 382/128

(58) Field of Classification Search
USPC .......................................... 705/2–3; 382/128
See application file for complete search history.

(56) References Cited

U.S. PATENT DOCUMENTS

| | | | |
|---|---|---|---|
| 4,972,264 A | 11/1990 | Bishop et al. | |
| 5,021,770 A | 6/1991 | Aisaka et al. | |
| 5,212,637 A | 5/1993 | Saxena | |
| 5,229,585 A | 7/1993 | Lemberger et al. | |

(Continued)

FOREIGN PATENT DOCUMENTS

| | | |
|---|---|---|
| EP | 0487110 | 5/1992 |
| WO | WO 03/046796 | 6/2003 |
| WO | WO 2005/003912 | 1/2005 |

OTHER PUBLICATIONS

PenRad, "Technologist Mammography System Handbook", Copyright 1995-2003 rev. Jul. 7, 2003.

(Continued)

*Primary Examiner* — Luke Gilligan
(74) *Attorney, Agent, or Firm* — Patterson Thuente Pedersen, P.A.

(57) ABSTRACT

A method and system for analyzing and retrieving tissue abnormality tracking data, providing a tool for a radiologist that includes a report summarizing the statistical frequency of diagnosed patients, both locally and nationally, with tissue region-of-interest classifications similar to the tissue images taken of the anatomy of an individual patient. In one embodiment, a computer aided diagnostic program can suggest region-of-interest attributes and classifications for user review. In one embodiment, user can select a seed area for computer aided diagnostic program analysis, the CAD analysis can suggest region-of-interest attributes and classifications. In yet another embodiment, the region-of-interest abnormality attributes suggested by the computer aided diagnostic program can be stored and compared with the user selected abnormality attributes and classifications. In one embodiment the images are of human breast tissue.

23 Claims, 25 Drawing Sheets

(56) References Cited

U.S. PATENT DOCUMENTS

| | | |
|---|---|---|
| 5,241,659 A | 8/1993 | Parulski et al. |
| 5,321,520 A | 6/1994 | Inga et al. |
| 5,325,478 A | 6/1994 | Shelton et al. |
| 5,343,390 A | 8/1994 | Doi et al. |
| 5,452,416 A | 9/1995 | Hilton et al. |
| 5,565,678 A | 10/1996 | Manian |
| 5,670,984 A | 9/1997 | Robertson et al. |
| 5,708,810 A | 1/1998 | Kern et al. |
| 5,719,567 A | 2/1998 | Norris |
| 5,917,929 A | 6/1999 | Marshall et al. |
| 5,940,188 A | 8/1999 | Kurozasa |
| 6,006,191 A | 12/1999 | DiRienzo |
| 6,047,257 A | 4/2000 | Dewaele |
| 6,176,429 B1 | 1/2001 | Reddersen et al. |
| 6,243,095 B1 | 6/2001 | Shile et al. |
| 6,246,782 B1 | 6/2001 | Shapiro et al. |
| 6,253,184 B1 | 6/2001 | Ruppert |
| 6,260,021 B1 | 7/2001 | Wong et al. |
| 6,311,419 B1 | 11/2001 | Inbar |
| 6,317,617 B1 | 11/2001 | Gilhuijs et al. |
| 6,347,241 B2 | 2/2002 | Burbank et al. |
| 6,347,299 B1 | 2/2002 | Holzman et al. |
| 6,349,143 B1 | 2/2002 | Hastings et al. |
| 6,355,024 B1 | 3/2002 | Small et al. |
| 6,434,262 B2 | 8/2002 | Wang |
| 6,587,830 B2 | 7/2003 | Singer |
| 6,614,921 B1 | 9/2003 | Chung et al. |
| 6,629,378 B2 | 10/2003 | Gustafson |
| 6,678,703 B2 | 1/2004 | Rothschild et al. |
| 6,766,297 B1 | 7/2004 | Lamer et al. |
| 6,785,358 B2 | 8/2004 | Johnson et al. |
| 6,831,648 B2 | 12/2004 | Mukherjee et al. |
| 6,901,156 B2 | 5/2005 | Giger et al. |
| 6,909,795 B2 | 6/2005 | Tecotzky et al. |
| 6,970,587 B1 | 11/2005 | Rogers |
| 7,081,976 B2 | 7/2006 | Harrington |
| 7,103,205 B2 | 9/2006 | Wang et al. |
| 7,124,760 B2 | 10/2006 | Wong |
| 7,146,031 B1 | 12/2006 | Hartman et al. |
| 7,184,582 B2 | 2/2007 | Giger et al. |
| 7,247,139 B2 | 7/2007 | Yudkovitch et al. |
| 7,308,126 B2 | 12/2007 | Rogers et al. |
| 7,321,668 B2 | 1/2008 | Horie et al. |
| 7,418,119 B2 * | 8/2008 | Leichter et al. ............... 382/128 |
| 7,616,801 B2 | 11/2009 | Gkanatsios et al. |
| 7,668,718 B2 | 2/2010 | Kahn et al. |
| 7,783,094 B2 | 8/2010 | Collins et al. |
| 8,014,576 B2 | 9/2011 | Collins et al. |
| 8,014,578 B2 | 9/2011 | Suryanarayanan et al. |
| 8,391,574 B2 | 3/2013 | Collins et al. |
| 8,606,497 B2 | 12/2013 | Doherty et al. |
| 2001/0041991 A1 | 11/2001 | Segal et al. |
| 2001/0043742 A1 | 11/2001 | Melen |
| 2002/0016718 A1 | 2/2002 | Rothschild et al. |
| 2002/0070973 A1 | 6/2002 | Croley |
| 2002/0107885 A1 | 8/2002 | Brooks et al. |
| 2002/0139019 A1 | 10/2002 | Gustafson |
| 2002/0161628 A1 | 10/2002 | Lane Poor, Jr. et al. |
| 2003/0007598 A1 | 1/2003 | Wang et al. |
| 2003/0013951 A1 | 1/2003 | Stefanescu et al. |
| 2003/0026503 A1 | 2/2003 | Kallergi et al. |
| 2003/0065705 A1 | 4/2003 | Santos-Gomez |
| 2003/0103663 A1 | 6/2003 | Li et al. |
| 2003/0110178 A1 | 6/2003 | Woods et al. |
| 2003/0174873 A1 | 9/2003 | Giger et al. |
| 2004/0034550 A1 | 2/2004 | Menschik et al. |
| 2004/0085443 A1 | 5/2004 | Kallioniemi et al. |
| 2004/0086158 A1 | 5/2004 | Leichter et al. |
| 2004/0101206 A1 | 5/2004 | Morimoto et al. |
| 2004/0111299 A1 | 6/2004 | Onishi |
| 2004/0122702 A1 | 6/2004 | Sabol et al. |
| 2004/0141661 A1 | 7/2004 | Hanna et al. |
| 2004/0181412 A1 | 9/2004 | Menhardt |
| 2004/0258287 A1 | 12/2004 | Gustafson |
| 2004/0258291 A1 | 12/2004 | Gustafson |
| 2005/0031177 A1 | 2/2005 | Langille et al. |
| 2005/0049497 A1 | 3/2005 | Krishnan et al. |
| 2005/0108060 A1 | 5/2005 | Sasano |
| 2005/0123185 A1 | 6/2005 | Balasubramanian et al. |
| 2005/0149360 A1 * | 7/2005 | Galperin ........................ 705/2 |
| 2005/0171430 A1 | 8/2005 | Zhang et al. |
| 2005/0177312 A1 | 8/2005 | Guerrant et al. |
| 2005/0216314 A1 | 9/2005 | Secor |
| 2005/0238216 A1 | 10/2005 | Yoden |
| 2005/0244041 A1 | 11/2005 | Tecotzky et al. |
| 2005/0244082 A1 | 11/2005 | Yamatake |
| 2006/0058603 A1 | 3/2006 | Dave et al. |
| 2006/0111937 A1 | 5/2006 | Yarger et al. |
| 2006/0147099 A1 | 7/2006 | Marshall et al. |
| 2006/0212317 A1 | 9/2006 | Hahn et al. |
| 2006/0257009 A1 | 11/2006 | Wang et al. |
| 2006/0274928 A1 | 12/2006 | Collins et al. |
| 2007/0003119 A1 | 1/2007 | Roehrig et al. |
| 2007/0038085 A1 | 2/2007 | Zhang et al. |
| 2007/0041623 A1 | 2/2007 | Roehrig et al. |
| 2007/0098243 A1 | 5/2007 | Gustafson |
| 2007/0118384 A1 | 5/2007 | Gustafson |
| 2007/0118399 A1 | 5/2007 | Avinash et al. |
| 2007/0122021 A1 | 5/2007 | Zingaretti et al. |
| 2007/0185732 A1 | 8/2007 | Hicks et al. |
| 2007/0211930 A1 | 9/2007 | Dolwick et al. |
| 2007/0274585 A1 | 11/2007 | Zhang et al. |
| 2008/0019581 A1 | 1/2008 | Gkanatsios et al. |
| 2008/0025592 A1 * | 1/2008 | Jerebko et al. ................ 382/132 |
| 2008/0130968 A1 | 6/2008 | Daw et al. |
| 2008/0162352 A1 | 7/2008 | Gizewski |
| 2008/0255849 A9 | 10/2008 | Gustafson |
| 2008/0267470 A1 | 10/2008 | Zhang et al. |
| 2008/0285825 A1 | 11/2008 | Zhang et al. |
| 2009/0093711 A1 * | 4/2009 | Hermosillo Valadez ...... 600/420 |
| 2009/0129644 A1 | 5/2009 | Daw et al. |
| 2009/0154782 A1 | 6/2009 | Zhang et al. |
| 2009/0165009 A1 | 6/2009 | Heffernan et al. |
| 2009/0171236 A1 | 7/2009 | Davies |
| 2009/0171871 A1 | 7/2009 | Zhang et al. |
| 2009/0185732 A1 | 7/2009 | Zhang et al. |
| 2009/0192823 A1 | 7/2009 | Hawkins et al. |
| 2009/0220138 A1 | 9/2009 | Zhang et al. |
| 2009/0238421 A1 | 9/2009 | Zhang et al. |
| 2009/0238422 A1 | 9/2009 | Zhang et al. |
| 2009/0310843 A1 | 12/2009 | Moriya |
| 2010/0086185 A1 | 4/2010 | Weiss |
| 2010/0280375 A1 | 11/2010 | Zhang et al. |
| 2011/0028825 A1 | 2/2011 | Douglas et al. |
| 2011/0087137 A1 | 4/2011 | Hanoun |
| 2011/0110576 A1 | 5/2011 | Kreeger et al. |
| 2011/0123073 A1 | 5/2011 | Gustafson |
| 2011/0123079 A1 | 5/2011 | Gustafson |
| 2012/0029936 A1 | 2/2012 | Hanoun |
| 2013/0016092 A1 | 1/2013 | Collins et al. |
| 2013/0343626 A1 | 12/2013 | Rico et al. |

OTHER PUBLICATIONS

AuntMinnie, "Confirma, PenRad Steamline Breast MRI Reporting". Nov. 27, 2007.

PenRad, "PenRad CAD Connectivity Module" Copyright 1997-2003 rev. Jul. 2, 2003.

AuntMinnie, "A Guide to Digital and Soft-Copy Mammography" Jul. 21, 2005.

Altera, "Medical Imaging Implementation Using FPGAs" Apr. 2006.

AuntMinnie, "PenRad Highlights Mammography Management Tools" Nov. 7, 2005.

PenRad, "PenRad Mammography Information System". Copyright 1998-2003. Jul. 2, 2003.

Internet Archive-PenRad.pdf files, as downloaded on Apr. 24, 2012.

Henry A. Swett, Pradeep G. Mutalik, Vladimir P. Neklesa, Laura Horvath, Carol Lee, Joan Richter, Irena Tocino, and Paul R. Fischer, Voice-Activated Retrieval of Mammography Reference Images, Journal of Digital Imaging, vol. 11, No. 2 May 1998: pp. 65-73.

GPCALMA: a Grid-based tool for Mammographic Screening. Authors: S. Bagnasco, U. Bottigli, P. Cerello, S.C. Cheran, P. Delogu, M.E. Fantacci, F. Fauci, G. Forni, A. Lauria, E. Lopez Torres, R.

(56) References Cited

OTHER PUBLICATIONS

Magro, G.L. Masala, P. Oliva, R. Palmiero, L. Ramello, G. Raso, A. Retico, M. Sitta, S. Stumbo, S. Tangaro, E. Zanon. HealthGrid Workshop 2004. arXiv.org.

Selenia—User Guide / Administrator Guide, P/N 9-500-0293, Rev. 1, Copyright 2002-2003.

PenRad, Mammography Information System awith R2 Checkmate Ultra CAD Connectivity Module. Copyright Sep. 18, 2002—Rev. Jun. 16, 2004.

Application and File History for U.S. Appl. No. 12/625,910, filed Nov. 25, 2009, inventor Gustafson, www.uspto.gov.

Application and File History of U.S. Appl. No. 11/443,742, filed May 31, 2006, Inventor Gustafson, www.uspto.gov.

Application and File History of U.S. Appl. No. 11/603,554, filed Nov. 22, 2006, Inventor Gustafson, www.uspto.gov.

Application and File History of U.S. Appl. No. 10/871,763, filed Jun. 17, 2004, Inventor Gustafson, www.uspto.gov.

Application and File History for U.S. Appl. No. 10/871,740, filed Jun. 17, 2004, inventor Gustafson, www.uspto.gov.

Application and File History of U.S. Appl. No. 12/625,926, filed Nov. 25, 2009, Inventor Gustafson, www.uspto.gov.

Application and File History of U.S. Appl. No. 12/625,898, filed Nov. 25, 2009, Inventor Gustafson, www.uspto.gov.

Definition of "SYNTHESIZE" freedictionary.com as downloaded Oct. 22, 2012.

Doi, "Current Status and future potential of computer-aided diagnosis in medical imaging" The British Journal of Radiology, 78. 2005.

Hsu et al.,"SPIRS: A Web-based Image Retrieval System for Large Biomedical Databases", 21 pages, Sep. 26, 2009.

\* cited by examiner

Right Breast Mammogram Abnormality Detailing | :Christine Jade Anderson, | 11/18/2009 20:28:38
Joanne W. Adamsick DOB: 09/01/1926 AGE: 83 F PID: 102828 SSN: 987654321

― Ab Type ―
Seen/US only
Possible
Multiple
Cluster of
Various

― Mass ―
Mass solid
Mass part solid
Mass skin

― Profile Ab ―
Shape
Irregular
Lobulated
Oval
Reniform
Round

Margin
Circumscribed
Indistinct
Microlobulated
Obscured
Spiculated

Density
High density
Low density
Equal density
Fat containing
Cent lucent

― Assoc Calc ―
Generic calcs
Amorphous
Branching
Coarse
Dystrophic
Eggshell
Fine
Heterogeneous
Indistinct
Large rodlike
Layering
Linear
Lucent centered
Milk of calcium
Pleomorphic
Punctate
Rim
Round
Skin
Spherical
Suture
Vascular

Calc Dist
Clustered
Diffuse
Grouped
Linear
Regional
Scattered
Segmental

― Assoc Findings ―
Archit distortion  Post surgical so
Axillary adenop   Skin involvemen
Brachy tube       Seroma
Bx clip           Skin lesion
Bx clips          Skin retraction
Chest wall inva   Skin thicken
Gold Seed         Surgical clip
Nipple retract    Surgical clips
Hematoma          Trab thicken ― Corresponds with ―
US     sz <US      sz > US
MRI    sz <MRI     sz > MRI
Palpated sz > palp  sz > palp
Pain   Tender    Incidental
Sc'tim Ductog.   Pst-op chg
Redness Concern  Skin marke ― Not Prev Seen On ―
Clinical exam MRI
Mammogram Ductogram
Ultrasound ― Special Circumstances ―
Addl Views      Dem By Prior
Confirm             Ultrasound
Do not Confirm      Aspiration
                    Biopsy
                    MRI Not sig If not palpable
Not on prev study
Visible ML only ― Consistent with ―
Likely represents
Most likely
Resembles
w/ differential dia
Abscess
Carcinoma
Carcinoma know
Cluster of cysts
Cyst
Cyst Oil
DCIS
Fat necrosis
Fibroadenoma
Fibroad. degener
Fibrocystic chang
Fibroglandular tis
Fibrosis
Hamartoma
Hematoma
Intramam node
Lipoma
Lymph node.
Mass Solid
Mastitis
Papillary lesion
Post surg scar
Post lumpec scar
Prev blopsy
Prev surgery
Prev trauma
Radical scar
Seroma
Skin lesion ― Impression & Recs ―
2 Benign
3 Probably benign
4 Suspicious abnorm
4a Susp ab - low
4b Susp ab - interme
4c Susp ab - modera
5 Highly suggestive
0 Needs addl evaluat
6 Known BX / postiv
Post BX / marker
N/A ― Changes ―
New
Not sig chg.
Stable
No long seen
Part removed
Incr in size
Decr in size
Less prom.
More prom.
Incr in number
Decr in number
Incr in calcs
Decr in calcs ― Size/Dist/Axis ―
Ab dimensions>
Titles on report
Parallel/skin
Perpendic/skin
In skin
In mammary
Hide clock on rpt
Hide location
Use in/out/up/lo

[Add Text] [OK] [Cancel] [Help] [Set Def]

Right Breast Mammogram Abnormality Detailing | :Christine Jade Anderson, | 11/18/2009 20:34:32
Joanne W. Adamsick DOB: 09/01/1926 AGE: 83 F PID: 102828 SSN: 987654321

─Ab Type─
Seen/US only
Possible
Multiple
Cluster of
Various

┌─Mass────────┐
│ Mass        │
│ Mass solid  │
│ Mass part solid │
│ Mass skin   │
└─────────────┘

─Profile Ab─
Shape
Irregular
Lobulated
Oval
Reniform
Round
Margin
Circumscribed
Indistinct
Microlobulated
Obscured
Spiculated
Density
High density
Low density
Equal density
Fat containing
Cent lucent ─Changes─
New
Not sig chg.
Stable
No long seen
Part removed
Incr in size
Decr in size
Less prom.
More prom.
Incr in number
Decr in number
Incr in calcs
Decr in calcs ─Assoc Calc─
Generic calcs
Amorphous
Branching
Coarse
Dystrophic
Eggshell
Fine
Heterogeneous
Indistinct
Large rodlike
Layering
Linear
Lucent centered
Milk of calcium
Pleomorphic
Punctate
Rim
Round
Skin
Spherical
Suture
Vascular
Calc Dist
Clustered
Diffuse
Grouped
Linear
Regional
Scattered
Segmental ─Assoc Findings─
Archit distortion  Post surgical so
Axillary adenop   Skin involvemen
Brachy tube      Seroma
Bx clip          Skin lesion
Bx clips         Skin retraction
Chest wall inva  Skin thicken
Gold Seed        Surgical clip
Nipple retract   Surgical clips
Hematoma         Trab thicken ─Corresponds with─
US       sz <US    sz > US
MRI      sz <MRI   sz > MRI
Palpated sz <palp  sz > palp
Pain     Tender    Incidental
Sc'tim   Ductog.   Pst-op chg
Redness  Concern   Skin marke ─Not Prev Seen On─
Clinical exam MRI
Mammogram Ductogram
Ultrasound ─Special Circumstances─
Addl Views    Dem By Prior
Confirm           Ultrasound
Do not Confirm    Aspiration
                  Biopsy
                  MRI
Not sig If not palpable
Not on prev study
Visible ML only ─Consistent with─
Likely represents
Most likely
Resembles
w/ differential dia
Abscess
Carcinoma
Carcinoma know
Cluster of cysts
Cyst
Cyst Oil
DCIS
Fat necrosis
Fibroadenoma
Fibroad. degener
Fibrocystic chang
Fibroglandular tis
Fibrosis
Hamartoma
Hematoma
Intramam node
Lipoma
Lymph node.
Mass Solid
Mastitis
Papillary lesion
Post surg scar
Post lumpec scar
Prev biopsy
Prev surgery
Prev trauma
Radical scar
Seroma
Skin lesion ─Impression & Recs─
<charge birads>
5 Highly suggestive
Unless previous sho
Ultrasound
Poss. Ultrasound
Biopsy
BX base on clinical
Clinical correlation
Diagnostic aspiration
FNA biopsy
MRI
MRI Biopsy
Needle loc. & surg b
US loc. & surg bx
Poss. core bx
Poss. stereo vac bx
Poss. US bx
Scintimammography
Stereotactic core bx
Surgical Consult
Surgical consult & bx
Ultrasound guided bx
Vacuum Bx ─Size/Dist/Axis─
Ab dimensions>
Titles on report
Parallel/skin
Perpendic/skin
In skin
In mammary
Hide clock on rpt
Hide location
Use in/out/up/lo Add Text | OK | Cancel | Help | Set Def m2:b2:t121
m32:b8:t180

Matching Statistical Information | Christine Jade Anderson, | 11/18/2009 20:28:10
Joanne W. Adamsick  DOB: 09/01/1926  AGE: 83  F  PID: 102828  SSN: 987654321

Matching Exam's Pathology Findings

| | Result | #Local | % of Result | #National | % of Result | Code | Finding |
|---|---|---|---|---|---|---|---|
| 1 | malign... | 20 | 20.62% | 14025 | 67.88% | ID | Invasive ductal carcinoma |
| 2 | malign... | 16 | 16.49% | 1700 | 8.23% | IL | Invasive lobular carcinoma |
| 3 | malign... | 9 | 9.28% | 48 | .23% | IPC | Invasive, Invasive papillary carcinoma |
| 4 | malign... | 4 | 4.12% | 324 | 1.57% | CC | Invasive, Mucinous carcinoma |
| 5 | malign... | 4 | 4.12% | 502 | 2.43% | CI | Comedocarcinoma (Intraductal) |
| 6 | malign... | 4 | 4.12% | 11 | .05% | CS | Carcinosarcoma |
| 7 | malign... | 4 | 4.12% | 614 | 2.97% | DCIS | Ductal carcinoma in situ |
| 8 | malign... | 4 | 4.12% | 30 | .15% | MC | Invasive, Medullary carcinoma |
| 9 | malign... | 3 | 3.09% | 336 | 1.63% | DS | Noninvasive, Intraductal carcinoma |
| 10 | malign... | 3 | 3.09% | 286 | 1.38% | II | Invasive and In-situ Cancer |
| 11 | malign... | 2 | 2.06% | 15 | .07% | ICC | Invasive cribriform carcinoma |
| 12 | malign... | 2 | 2.06% | 20 | 1% | INC | Inflammatory Carcinoma |
| 13 | malign... | 2 | 2.06% | 17 | .08% | LS | Noninvasive, Lobular carcinoma in situ |
| 14 | malign... | 2 | 2.06% | 115 | .56% | LY | Lymphoma |
| 15 | malign... | 2 | 2.06% | 7 | .03% | MDC | Multifocal Intraductal Carcinoma |
| 16 | malign... | 1 | 1.03% | 1117 | 5.41% | * | Other malignant |
| 17 | malign... | 1 | 1.03% | 44 | .21% | AP | Apocrine Carcinoma |
| 18 | malign... | 1 | 1.03% | | % | CCH | Carcinoma in children |
| 19 | malign... | 1 | 1.03% | | % | CEB | Carcinoma in ectopic breast |
| 20 | malign... | 1 | 1.03% | | % | COT | Cartilaginous and Osseous |
| 21 | malign... | 1 | 1.03% | 112 | .54% | DCH | Intraductal carcinoma, high grade |
| 22 | malign... | 1 | 1.03% | | % | FS | Mesenchymal Tumors, Fibrosarcoma |
| 23 | malign... | 1 | 1.03% | 3 | .01% | IC | Intracystic Carcinoma |
| 24 | malign... | 1 | 1.03% | 80 | .39% | ICP | Intraductal papillary Carcinoma |
| 25 | malign... | 1 | 1.03% | 28 | .14% | MB | Metastatic Lesion to the Breast |
| 26 | malign... | 1 | 1.03% | | % | MBL | Metastatic Lung Cancer to the Breast |

[ Print List ]   [ Show Exams ]   [ Exit ]   [ Help ]

Fig. 8

| | Sel | Date | Description | Patient Name | PID | Rad Name |
|---|---|---|---|---|---|---|
| 1 | ☐ | 09/12/1995 | Mammography Examination | Bruns, Joni J | 223241609 | Daskair, Tom, Md Re |
| 2 | ☐ | 12/14/1995 | Mammography Examination | Lee, Ann P | 73745 | Pobble, Robert, M.D |
| 3 | ☐ | 12/14/1995 | Mammography Examination | Lee, Julie P | 3755 | Anderson, Christine, |
| 4 | ☐ | 05/20/1996 | Mammography Examination | Dibernardo, Nancy O | 725717 | Carsen, Leo, MD |
| 5 | ☐ | 05/28/1996 | Mammography Examination | Nauve, Ella J | 9622857 | Anderson, Christine, |
| 6 | ☐ | 10/29/1996 | Mammography Examination | Mann, Ruthanne M | 56715 | Anderson, Christine, |
| 7 | ☐ | 03/09/2000 | Mammography Examination | Jensen, Anita W | 43460 | Anderson, Christine, |
| 8 | ☐ | 04/01/2000 | Mammography Examination | Kachel, Luella I | 223243960 | Anderson, Christine, |
| 9 | ☐ | 07/14/2000 | Mammography Examination | Cacy, Nila E | 0235 | Anderson, Christine, |
| 10 | ☐ | 07/23/2000 | Mammography Examination | Qq, Adele R | 323138 | Anderson, Christine, |
| 11 | ☐ | 07/06/2001 | Mammography Examination | Demcho, Andrene K | 743407 | Anderson, Christine, |
| 12 | ☐ | 12/09/2002 | Mammography Examination | Zamiska, Mary D | 54275 | Anderson, Christine, |
| 13 | ☐ | 08/18/2005 | Mammography Examination | Black, Nancy J | 223246201 | Anderson, Christine, |
| 14 | ☐ | 09/12/2005 | Mammogram | Landsberg, Deborah | 3483 | Anderson, Christine, |
| 15 | ☐ | 09/15/2005 | Mammogram | Soenpaa, Adeline K | 8823544 | Anderson, Christine, |
| 16 | ☐ | 10/17/2005 | Mammogram | Christian, Judy P | 223242014 | Anderson, Christine, |
| 17 | ☐ | 10/18/2005 | Mammogram | Kimbe, Ann T | 743584 | Anderson, Christine, |
| 18 | ☐ | 03/27/2006 | Mammography Examination | Bach, Gwendolyn V | 223239966 | Anderson, Christine, |
| 19 | ☐ | 03/27/2006 | Mammogram | Beal, Myra E | 223246122 | Anderson, Christine, |
| 20 | ☐ | 08/02/2006 | Mammogram | Adamski, Helen H | 223240137 | Zippy, Gregory, M.D. |

Matching Statistical Information : Christine Jade Anderson, Penrad Main Clinic | 11/18/2009 20:28:10
Joanne W. Adamsick DOB: 09/01/1926 AGE: 83 F PID: 102828 SSN: 987654321
Exams w/pathology: ID - Invasive ductal carcinoma View patient priors | Print List | Send Images to Viewstation | ☐ Show all exams with finding - unfiltered by procedure type or selections | Show Findings | Exit | Help

Fig. 9

ComParisons and Prior Exams : Christine Jade Anderson, Penrad Main Clinic | 11/18/2009 20:30:50
Julie P. Lee  DOB: 12/10/1930  AGE: 78 F  PID: 3755

Select Exam Report for Review

| | Date | Description | Recall | Ris Proc# |
|---|---|---|---|---|
| 1 | 02/17/2004 | Bilateral Screening Mammography :birads 1 | 2 year screening | |
| 2 | 11/19/2002 | Bilateral Screening Mammography :birads 1 | 2 year screening | |
| 3 | 01/09/1996 | Bilateral Diagnostic Mammography :birads 1 | 1 year screening | |
| 4 | 12/14/1995 | Pathology | No Recall (discretio.. | |
| 5 | 12/14/1995 | Bilateral Screening Mammography :birads 1 | Immediate follow-up | |

View Full  Preview  Print  Send to Viewstation  Create CD  Notes-Yes  Exit  Help

Fig. 10

Preview   :Christine Jade Anderson, Penrad Main Clinic   11/18/2009 20:33:23
Julie P. Lee   DOB: 12/10/1930   AGE: 78 F   PID: 3755

Golden Valley, Minnesota 55343

Fax: (763) 555-5555

BILATERAL SCREENING MAMMOGRAM: 12/14/1995
Comparison is made to exam dated: 4/24/1993 East Memorial Center.
The tissue of both breasts is predominantly fatty.
There is a 6 cm round high density mass with a spiculated margin in the right breast at 12 o'clock in the posterior depth as palpated. Compared to previous films, this mass is new.
No significant masses, calcifications, or other findings are seen in the left breast.
IMPRESSIONS: SUSPICIOUS OF MALIGNANCY
The mass in the right breast is suspicious of malignancy. A clinical correlation is recommended for the mass.

REPORT REFLECTS CURRENT DEMOGRAPHICS AND CODING OS OF 11/18/2009

The patient has been or will be contacted.

Dr. Christine Jade Anderson M.D.
cja/penrad:12/14/1995 13:17:57

Imaging Technologist: Rabbi Patty A. Ferdickson RT(R)(M), Penrad Main Clinic
letter sent: Biopsy Required
Mammo BI-RADS: 4 Suspicious abnormality

Print Copy     Close

| Result | National | Percent of | Code | Finding |
|---|---|---|---|---|
| malignant | 36 | 22.2% | CI | Comedocarcinoma (Intraductal) |
| malignant | 32 | 19.8% | ID | Invasive ductal carcinoma |
| malignant | 24 | 14.8% | * | Other malignant |
| malignant | 23 | 14.2% | DCIS | Ductal carcinoma in situ |
| malignant | 13 | 8.0% | II | Invasive and In-situ Cancer |
| malignant | 10 | 6.2% | DCH | Intraductal carcinoma, high grade |
| malignant | 7 | 4.3% | DCC | Intraductal comedocarcinoma with necrosis |
| malignant | 6 | 3.7% | DS | Noninvasive, Intraductal carcinoma |
| malignant | 6 | 3.7% | PC | Papillary Carcinoma in-Situ |
| malignant | 5 | 3.1% | DCL | Intraductal carcinoma, low grade |
| benign | 37 | 14.0% | FA | Fibroadenoma |
| benign | 37 | 14.0% | DHU | Ductal Hyperplasia, Usual |
| benign | 36 | 13.6% | AD | Adenosis |
| benign | 35 | 13.3% | * | Other benign |
| benign | 27 | 10.2% | FC | Fibrocystic changes |
| benign | 19 | 7.2% | ADH | Hyperplasia, Atypical ductal |
| benign | 16 | 6.1% | AM | Apocrine Metaplasia |
| benign | 10 | 3.8% | SA | Adenosis, Sclerosing tumor |
| benign | 10 | 3.8% | * | Fibrosis |
| benign | 9 | 3.4% | BCL | Benign calcifications |
| benign | 9 | 3.4% | BC | Cysts |
| benign | 4 | 1.5% | FNS | Fibroadenoma, NOS (not otherwise specified) |
| benign | 3 | 1.1% | NOS | - high risk |
| benign | 3 | 1.1% | FAL | Fibroadenolipoma |
| benign | 3 | 1.1% | IF | Inflammatory pseudotumors, Inflammation |
| benign | 3 | 1.1% | IP | Intraductal Papilloma |
| benign | 3 | 1.1% | FN | Inflammatory pseudotumors, Fat necrosis |

Matching Pathology from PenRad Statistical Database

● Mammo - Mass ○ Mammo - Calc ○ MRI ○ US

CALC TYPE
☐ Generic calcs
☐ Amorphous
☐ Branching
☐ Coarse
☐ Dystrophic
☐ Eggshell
☐ Fine
☐ Heterogeneous
☐ Indistinct
☐ Large rodlike
☐ Layering
☐ Linear
☐ Lucent-centered
☐ Milk of calcium
☐ Pleomorphic
☐ Punctate
☐ Rim
☐ Round
☐ Skin
☐ Spherical
☐ Suture
☐ Vascular

CALC DIST
☐ Clustered
☐ Diffuse
☐ Grouped
☐ Linear
☐ Regional
☐ Scattered
☐ Segmental

ASSOC FINDING
☐ Archit distortion
☐ Axillary adenop
☐ Chest wall invas
☐ Nipple retract
☐ Hematoma
☐ Skin Involvement
☐ Seroma
☐ Skin lesion
☐ Skin retraction
☐ Skin thicken
☐ Trab thicken

Profile Matches
Total: 757
Malignant: 152
Benign: 264
No BX: 331
BX profile
% Malignant: 38
% Benign: 62

Fig. 14

○ Mammo - Mass ○ Mammo - Calc ○ MRI ● US

SHAPE
○ Irregular
○ Lobulated
○ Oval
● Round
○ N/A

MARGIN
○ Irregular
○ Circumscribed
● Indistinct
○ Intraductal extension
○ Irregular
○ Lobulated
○ Microlobulated
○ Smooth
○ N/A

WALL
○ Irregular internal wall
○ Septated internal wall
○ Smooth internal wall
○ Thickened wall
● N/A

ORIENTATION
○ Parallel/skin
○ Perpendic/skin
● N/A

BOUNDARY
○ Abrupt boundary
○ Echogenic boundary
○ Hypherechoic rim
○ Well defined boundary
● N/A

HILUIM
○ Fatty hilum
○ No fatty hilium
● N/A

ECHO
☐ w/internal echoes
☐ w/posterior enhancement
☑ w/posterior shadowing

INTERNAL ECHO
☐ Anechoic
☑ Hypoechoic
☐ Hyperechoic
☐ Isoachoic
☐ Mixed echogenic
☐ Septated

ASSOC FINDING
☐ Archit distortion
☐ Chest wall invas
☐ Cooper distorted
☐ Cooper thicken
☐ Edema
☐ Edema adj
☐ Pect musc invas
☐ Pect musc tent
☐ Skin involvement
☐ Skin retraction
☐ Skin thicken
☐ BX clip
☐ BX clips
☐ Calcification
☐ Micro calcs
☐ Rim calcs
☐ Milk of calcium
☐ Calc in mass
☐ Calc on mammo
☐ Calc Not on mam

Profile Matches
Total: 39
Malignant: 6
Benign: 18
No BX: 15
BX profile
% Malignant: 25
% Benign: 75

Matching Pathology from PenRad Statistical Database

| Result | National | Percent of | Code | Finding |
|---|---|---|---|---|
| malignant | 6 | 100.0% | ID | Invasive ductal carcinoma |
| benign | 6 | 33.3% | * | Fibrosis |
| benign | 3 | 16.7% | DHU | Ductal Hyperplasia, Usual |
| benign | 3 | 16.7% | NOS | benign |
| benign | 3 | 16.7% | FA | Fibroadenoma |
| benign | 3 | 16.7% | BC | Cysts |

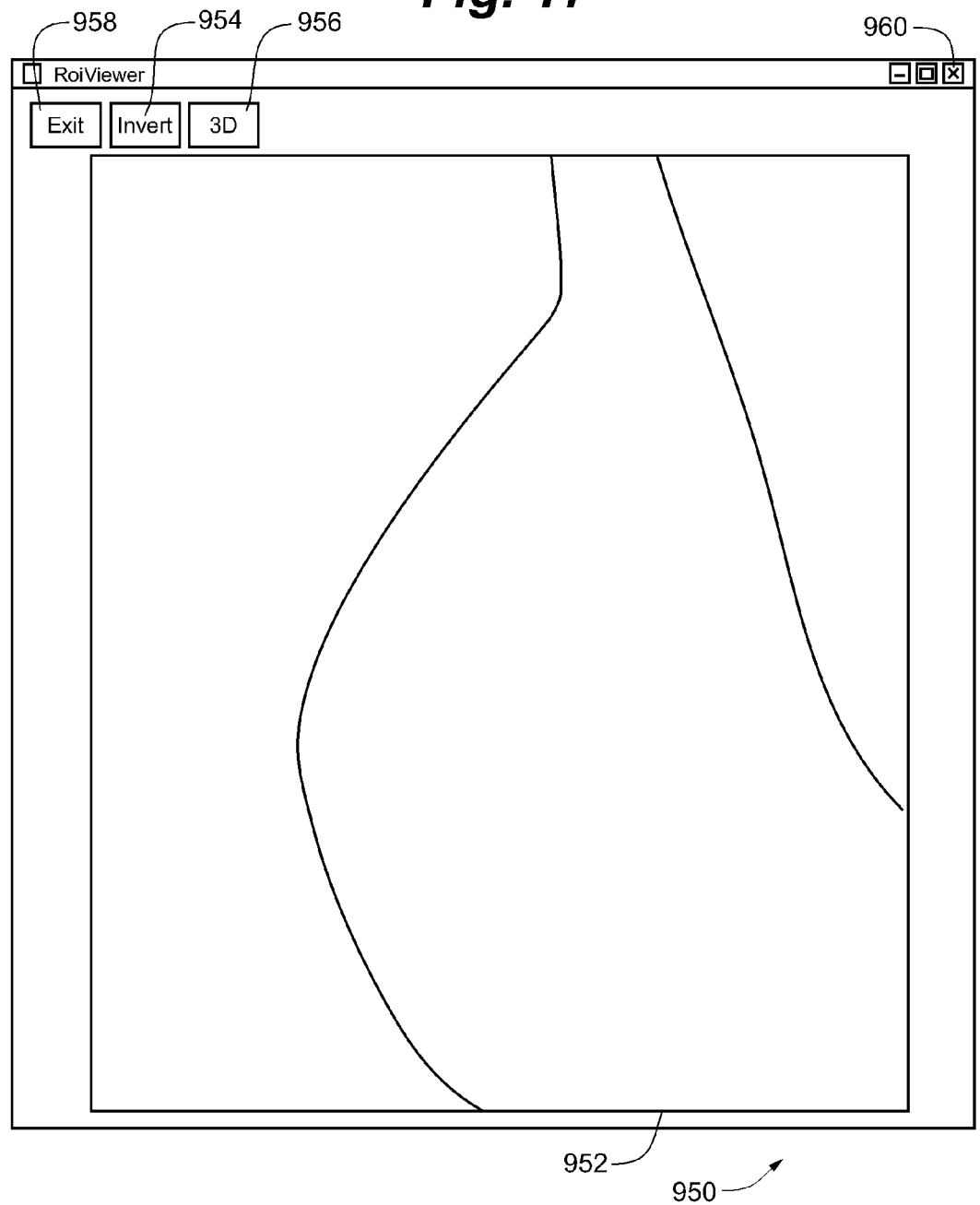

Fig. 18

| Scheduled Patients | | .Christine Jade Anderson, Able Clinic | | | 3/6/2009 08:19:08 |
|---|---|---|---|---|---|
| Pos | Status | Patient Name | PID | DOB | Date | Procedure |
| 813 | Imaged | Mertens, Bess W | 744300 | 07/12/1922 | 03/05/2009 | Screening, bilateral, digital, w... |
| 814 | Imaged | Mion, Gloria A | 748754 | 08/08/1938 | 03/05/2009 | Screening, bilateral, digital, w... |
| 815 | Imaged | Molly, Gladys A | 823381 | 04/05/1936 | 03/05/2009 | Screening, bilateral, digital, w... |
| 816 | Imaged | Oliver, Ada C | 743023 | 05/16/1909 | 03/05/2009 | Screening, bilateral, digital, w... |
| 817 | Imaged | Olson, Jeanette I | 109901 | 04/06/1944 | 03/05/2009 | Screening, bilateral, digital, w... |
| 818 | Imaged | O'Shea, Joan Q | 750275 | 08/07/1943 | 02/26/2009 | Asymptomatic diagnostic, bil... |
| 819 | Imaged | Pandoli, Lisa R | 752334 | 10/05/1948 | 02/26/2009 | Screening, bilateral, digital, w... |
| 820 | Imaged | Peterson, Ruby T | 8424032 | 11/28/1934 | 03/05/2009 | Screening, bilateral, digital, w... |
| 821 | Imaged | Phillips, Helen L | 748989 | 02/08/1939 | 03/05/2009 | Screening, bilateral, digital, w... |
| 822 | Imaged | Powell, Marlene O | 823241 | 03/08/1938 | 03/05/2009 | Screening, bilateral, digital, w... |
| 823 | Imaged | Radford, Kathleen A | 00195525 | 12/12/1945 | 03/05/2009 | Screening, bilateral, digital, w... |
| 824 | Imaged | Rasmussen, Arleen H | 743782 | 12/12/1920 | 03/05/2009 | Screening, bilateral, digital, w... |
| 825 | Imaged | Reising, Virginia H | 729591 | 12/24/1935 | 03/05/2009 | Screening, bilateral, digital, w... |
| 826 | Imaged | Renfrow, Marsha N | 223245036 | 05/05/1935 | 03/05/2009 | Screening, bilateral, digital, w... |
| 827 | Imaged | Renwick, Palma S | 423203 | 03/22/1925 | 03/05/2009 | Screening, bilateral, digital, w... |
| 828 | Imaged | Restemayer, Naomi T | 823204 | 06/28/1937 | 03/05/2009 | Screening, bilateral, digital, w... |
| 829 | Imaged | Shapiro, Joy R | 730143 | 12/23/1952 | 03/05/2009 | Screening, bilateral, digital, w... |
| 830 | Imaged | Shepard, Adeline A | 823448 | 09/08/1925 | 03/05/2009 | Screening, bilateral, digital, w... |
| 831 | Imaged | Shoup, Rebecca H | 730199 | 07/09/1954 | 03/05/2009 | Screening, bilateral, digital, w... |
| 832 | Imaged | Slann, Sophia E | 102144 | 01/04/1955 | 03/05/2009 | Screening, bilateral, digital, w... |
| 833 | Imaged | Singer, Grace E | 748800 | 06/08/1938 | 03/05/2009 | Screening, bilateral, digital, w... |
| 834 | Imaged | Skully, Sally E | 56760 | 09/07/1923 | 03/05/2009 | Screening, bilateral, digital, w... |

Filter By: Screening Mamma - Digital

Print List | Edit Film Position
Sort By: Name
Show All Owners
Fetch Images: All | Selected PreExam | Set Auto Track | Set Status | Delete Preview Exam Report: Preview
Refresh | Edit Patient | Appointments | Imaging | Close | Next Films | Help

| | Comparisons and Prior Exams | :Christine Jade Anderson, Penrad Main Clinic | 3/6/2009 09:51:24 |
| | Diane N. Adams DOB: 06/18/1939 AGE: 69 F PID: 83224091 SSN: 345555555 | | |

Prior Imaging Dates
- 4: 02/26/2008 Screening, bilateral film(s), Perrad Main Clinic, Plymouth, MN
- 5: 09/28/2007 Screening, mammogram, bilateral film(s), Able Clinic, Plymouth, MN
- 6: 04/27/2007 Screening, mammogram, bilateral film(s), Penrad Main Clinic, Plymouth, MN
- 7: 02/23/2007 Screening, mammogram, bilateral film(s), Penrad Main Clinic, Plymouth, MN
- 8: 10/05/2006 Screening, mammogram, bilateral film(s), Penrad Main Clinic, Plymouth, MN
- 9: 05/02/2006 Screening, mammogram, bilateral film(s), Penrad Main Clinic, Plymouth, MN
- A: 02/15/2006 Screening, mammogram, bilateral film(s), Penrad Main Clinic, Plymouth, MN
- B: 08/16/2005 Screening, mammogram, bilateral film(s), Penrad Main Clinic, Plymouth, MN

[ Verify Archive ] [ Request Scan ] [ Remove ] [ Check In/Out ]

Add Generic Imaging Date
Location
[ Change Location ] [ Clear ] [ This Location ] Date: [ _/_/_ ] [?]  [ Add to History ]

Exam/Film Type
Mammogram
Ultrasound
Breast MRI

[ Notes-Yes ]
[ Bone Density ]

Select Exam Report for Review

| # | Date | Description | Recall | Ris Proc# |
|---|------|-------------|--------|-----------|
| 1 | 10/06/2008 | Bilateral Screening Mammography :birads 1 | 1 year screening | |
| 2 | 04/28/2008 | Bilateral Screening Mammography :birads 1 | 1 year screening | |
| 3 | 02/26/2008 | Bilateral Screening Mammography :birads 1 | 1 year screening | |
| 4 | 09/28/2007 | Bilateral Screening Mammography :birads 2 | 1 year screening | |
| 5 | 04/27/2007 | Bilateral Screening Mammography :birads 2 | 1 year screening | |
| 6 | 02/23/2007 | Right Stereotactic Core Biopsy | No Recall - no msg | |
| 7 | 02/23/2007 | Bilateral Screening Mammography :birads 4b | No Recall - no msg | |
| 8 | 10/05/2006 | Bilateral Screening Mammography :birads 1 | 1 year screening | |

[ View Full ] [ Preview ] [ Print ] [ Amend ] [ Resolve ] [ Unresolve ] [ Send to Viewstation ] [ Delete ] [ Edit ]

[ Create CD ]
[ OK ]
[ Cancel ]
[ Help ]

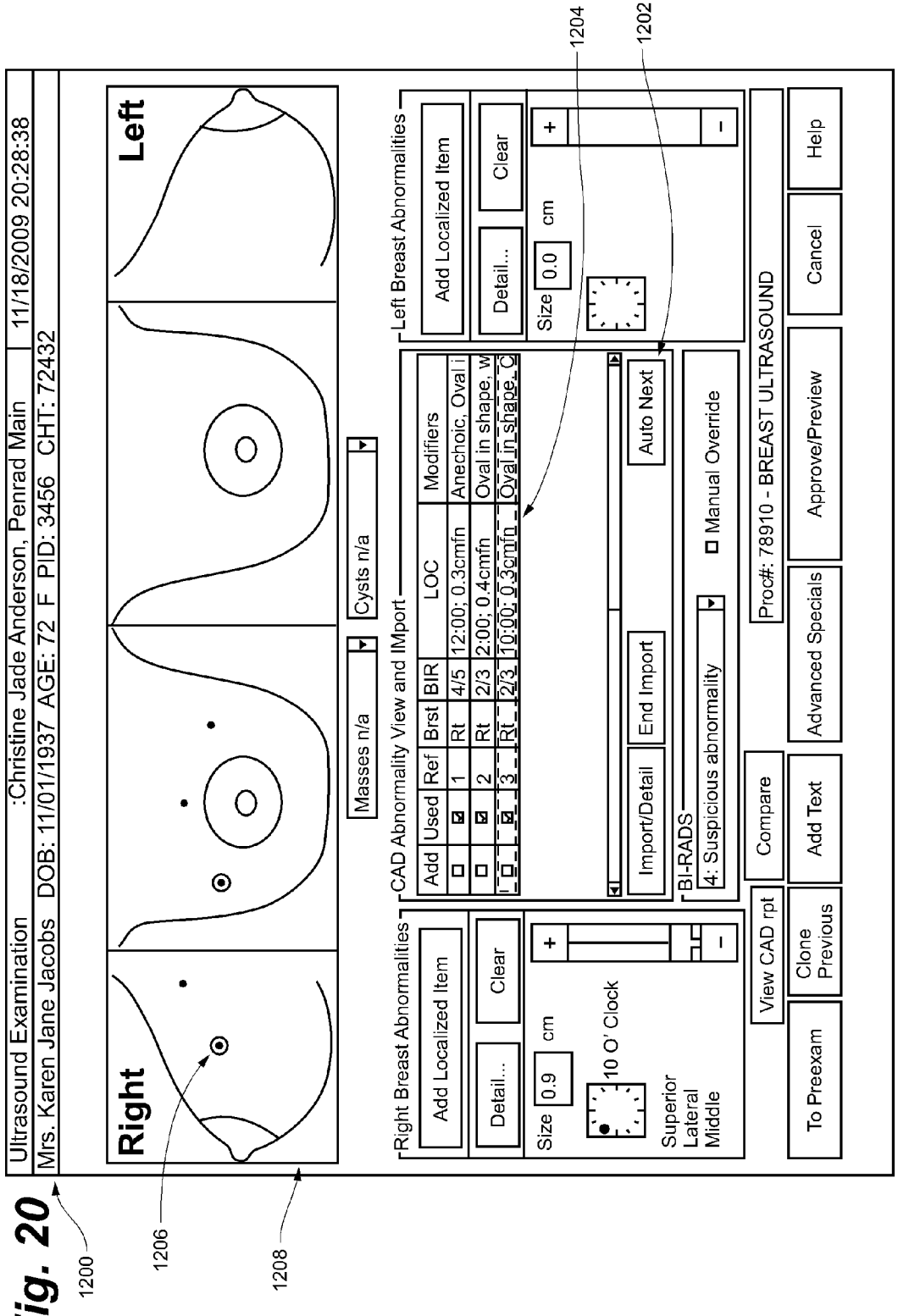

Fig. 21

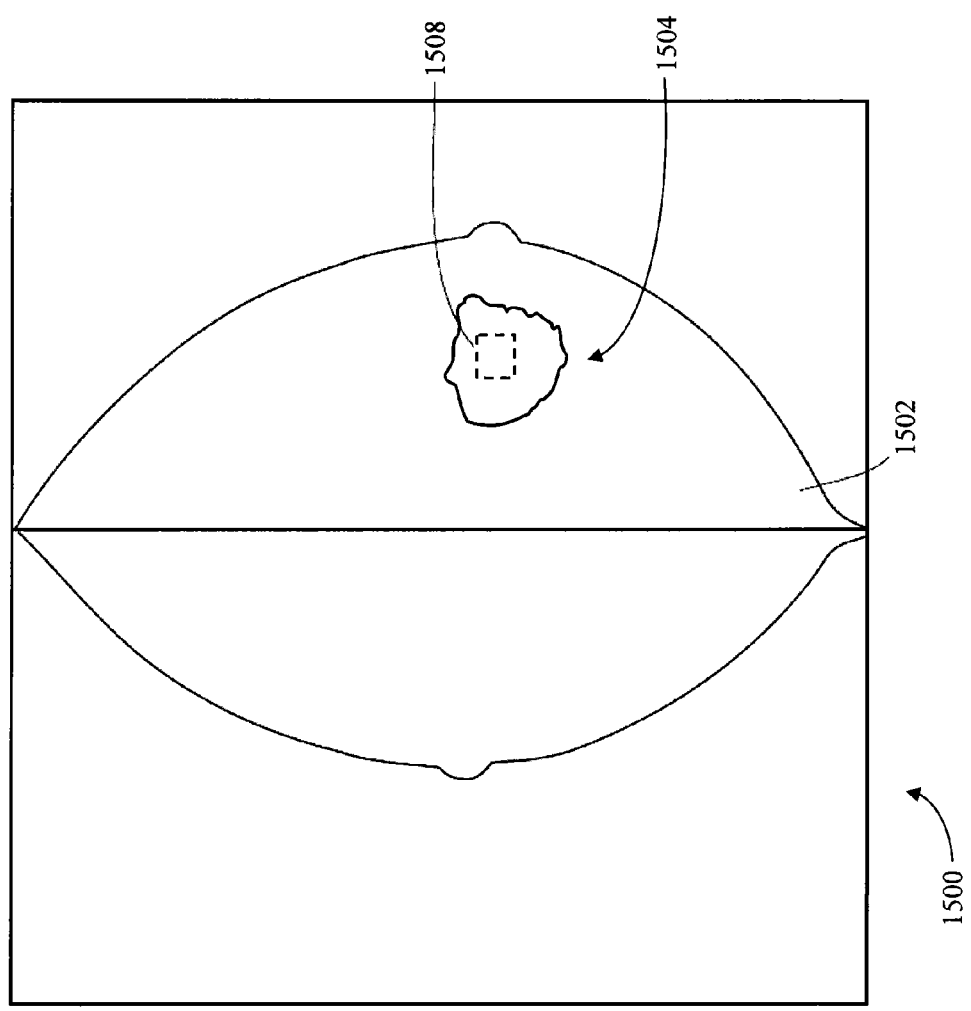

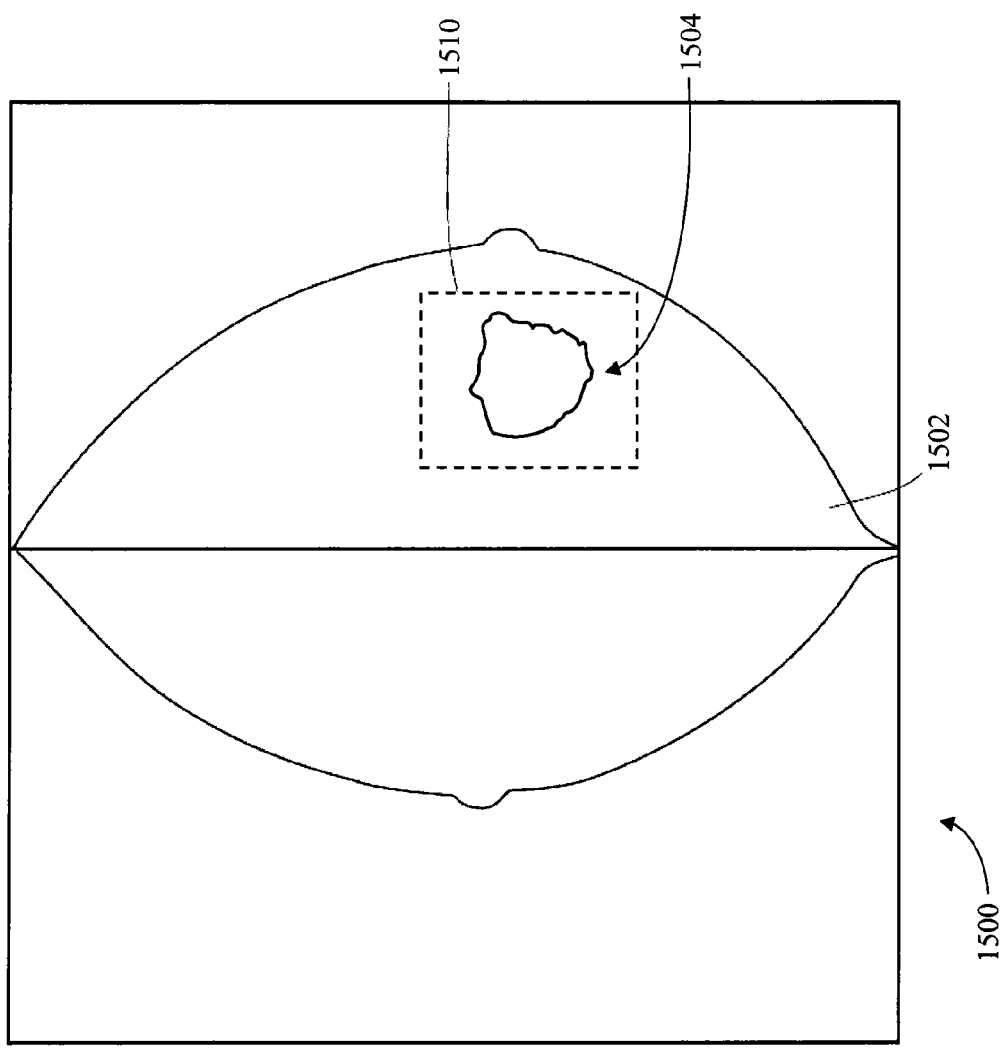

MAMMOGRAPHY INFORMATION SYSTEM

RELATED APPLICATIONS

This application is a Continuation-In-Part of U.S. patent application Ser. No. 12/625,898, filed Nov. 25, 2009, which claims the benefit of U.S. Provisional Application No. 61/282,000, entitled "MAMMOGRAPHY INFORMATION SYSTEM" and filed Nov. 24, 2009, which are incorporated herein by reference in its entirety.

The following co-pending patent applications of common assignee contain some common disclosure: "Multiple Modality Mammography Image Gallery and Clipping System," U.S. patent application Ser. No. 12/625,926 and "Mammography Statistical Diagnostic Profiler and Prediction System," U.S. patent application Ser. No. 12/625,910, filed Nov. 25, 2009, which are incorporated herein by reference in their entireties. A copy of each of the above-identified related applications is attached hereto as Appendix A and Appendix B, respectively.

TECHNICAL FIELD

The invention relates to management of images and medical data, and more specifically to patient data and breast tissue images originating from multiple modalities.

BACKGROUND

Historically, interpretation and diagnosis of mammograms and other medical image analysis has been performed using hardcopy x-ray films viewed on an alternator that typically allows x-ray films to be illuminated and masked for diagnostic viewing. Newer technology allows a radiologist or other medical professional to view mammograms and other diagnostic images electronically on high-resolution monitors. These images can also be digitally stored and transmitted across secure networks for archiving or review by other professionals.

A radiologist generally begins his or her review process by reviewing a patient's background information relevant to a radiology study, such as a patient's name, age, and any applicable medical conditions or risk factors. After reviewing the background information, the radiologist views multiple images created by radiological, X-ray, computed tomography (CT), ultrasound, magnetic resonance imaging (MRI), tomosynthesis, or other imaging technique of the patient's breast, or other organ, and dictates or uses a computerized information system to track findings, create reports, and make recommendations for future examinations. Such findings can include information pertaining to tissue density, the presence of masses, cysts, calcifications and other abnormalities, or any other breast tissue characteristics.

While there has been recent debate regarding the frequency at which women should undergo regular mammogram screenings, and at what age such screenings should begin, it is unlikely that the relatively quick and typically effective practice of mammography screening for breast cancer will disappear completely. Accordingly, there will continue to be a need for radiologists to view and interpret the images generated from patient examinations and screenings. Because the risk of breast cancer threatens the lives of many women, especially those over age 40, radiologists are often inundated with large numbers of mammogram images that must be viewed and, if abnormalities are present, categorized in order to determine if further examination is required. The developments in advanced patient imaging techniques, such as MRI, are also increasing the raw number of images that a radiologist can review. Therefore, there is an ongoing need to improve the speed and efficiency of the radiologist's review of the mammogram images, without sacrificing accuracy, and with the smallest number of false-positive diagnoses. Additionally, given that mammogram screenings are performed periodically, such as annually or biannually, once screening begins for a particular individual, there is also a need to manage, track and analyze data taken over a period of years or decades for that individual.

One example of a computerized mammography information system (MIS) to review patient images is the PenRad Mammography Information System available from PenRad. This system provides for the digital presentation of patient data.

Legislation has mandated that mammography facilities track positive mammography findings and correlate such findings with biopsy results, maintain statistics for mammography medical outcome and analysis audits on each physician, and provide direct written notification to all patients of their exam results. The generation and correlation of this data is maintained locally by each medical center for each patient.

One system for categorizing this information is the Breast Imaging-Reporting and Data System (BI-RADS) published by the American College of Radiology (ACR). BI-RADS provides a system of mammography assessment categories in the form of standardized codes assigned by a radiologist during or after the viewing and interpretation of a medical image. BI-RADS allows for concise and unambiguous understanding of patient records between multiple radiologists and medical facilities. Consequently, a large number of mammogram images, biopsy results, and diagnosis statistics are potentially available in a patient-anonymous format, in compliance with the Health Insurance Portability and Accountability Act of 1996 (HIPAA).

Recently, Digital Imaging and Communications in Medicine (DICOM) systems have become the accepted format for medical imaging systems. This format provides for the distribution and viewing of medical studies and images across a variety of platforms. The use of DICOM has, among other things, enabled industry compatibility and improved workflow efficiency between imaging and other information systems located in various healthcare environments. Currently, the DICOM standard is an 18-part publication, PS 3.1-2008 through PS 3.18-2008 describing a standard for digital imaging and communications in medicine developed by the American College of Radiology (ACR) and the National Electrical Manufacturers Association (NEMA), which is hereby incorporated by reference in its entirety. Among other elements, the DICOM standard provides a method of uniquely numbering any image or other information object to facilitate the unambiguous identification of images or information objects as they are viewed or manipulated in a system or transported across a network.

Conventional imaging systems enable a DICOM server to provide medical images across a network to various DICOM compatible clients on the network. Some examples of DICOM clients include picture archiving and communications systems, softcopy workstations, computer-aided diagnosis (CAD) systems, DICOM compatible CD or DVD burners, and other network system devices known to those skilled in the art. One example of a standards-based medical imaging environment is disclosed in U.S. Pat. No. 6,909,795, to Tecotzky et al., incorporated herein by reference.

Computer Aided Diagnosis systems, such as the R2 Digital CAD system by Hologic, Inc., or systems available from iCAD, Inc. of Nashua, N.H., and Medipattern Corp. of Toronto, Ontario, can produce various image feature descriptions by extracting attributes of one or more regions of interest (ROI) from a DICOM SR file or other file format containing a radiographic image (e.g. a mammogram). This information can include size, location and attributes of a region of interest including, but not limited to, shape, margins, abnormality structure type, echo patterns, and the like. Many of these ROIs and associated features are false marks (i.e., not relevant to a diagnosis), or if the region for processing has been manually been selected for processing may contain various attributes or features that are not relevant or incorrect. An exemplary CAD system is disclosed in U.S. Pat. No. 7,783,094 to Collins et al., incorporated herein by reference.

SUMMARY

Embodiments relate to systems and methods of retrieving and analyzing patient data in a mammography information system as part of or in conjunction with the diagnosis and interpretation of patient mammography images that substantially meet the aforementioned needs of the industry. In an example embodiment, the system is capable of retrieving, presenting, and analyzing patent images originating from a variety of modalities.

In an embodiment, a configurable mammography diagnostic system comprises a plurality of electronic displays, at least one of the plurality of electronic displays configured to display a breast tissue image having at least one region of interest, a database including a plurality of existing categorizations of at least one known region of interest in at least one of a plurality of breast tissue images, a graphical user interface presented on at least one of the plurality of electronic displays and including an anatomical diagram on which the at least one region of interest can be marked, a detailing button linked to a screen configured to present a plurality of possible characteristics according to which a manual current categorization of a region of interest in the breast tissue image can be defined, and a profiler display button configured to present statistical information related to a comparison of the manual current categorization with the existing categorizations, a clipping tool with which a portion of the breast tissue image displayed on at least one of the plurality of electronic displays can be selected as a second image, the second image displayable on at least one of the plurality of electronic displays as a subset of the breast tissue image, and a processing engine configured to link the second image to the breast tissue image, store the second image in an image database, and to associate the second image with a corresponding region of interest marked on the anatomical diagram.

In an embodiment, a method for managing patient mammography data comprises obtaining a plurality of breast tissue images selected from the group consisting of an X-ray image, a CT image, an MRI image, an ultrasound image, and a pathology image, identifying a region of interest in at least one of the plurality of breast tissue images, obtaining a categorization of the region of interest according to an established lexicon, comparing the categorization with a database of existing categorizations and presenting a diagnostic indicator based on the comparing, storing a selected region of the at least one of the plurality of breast tissue images as a second image, mapping the second image to a storage location of the at least one of the plurality of breast tissue images, and associating the selected region with the categorized region of interest.

In an embodiment, a mammography information system comprises at least one electronic display, a graphical user interface presented on the at least one electronic display and configured to present data and information related to a patient, the graphical user interface comprising an image gallery configured to display thumbnail representations of a plurality of images that form a portion of the data and information, the plurality of images selectable from X-ray images, CT images, MRI images, ultrasound images, pathology images and document images, and a database operable to store the thumbnail representations of the plurality of images.

In an embodiment, a configurable mammography diagnostic system comprises a reporting system that automates the importation and selection of one or more ROI and associated ROI descriptions in an image, generated by a CAD image analysis module of the image, for inclusion in (or exclusion from) a narrative report generation and the cataloging of the findings describing each ROI.

In one embodiment, a computer aided diagnostic program can suggest region-of-interest classifications for user review. In one embodiment, user can select a seed area of an image for computer aided diagnostic program analysis, the CAD analysis can suggest region-of-interest attributes and classifications based on the seed area provided by the user. In yet another embodiment, the region-of-interest abnormality attributes and classifications suggested by the computer aided diagnostic program can be stored and compared with the user selected abnormality attributes and classifications.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The embodiments of the present invention may be more completely understood in consideration of the following detailed description of various embodiments in connection with the accompanying drawings, in which:

FIG. 2 is an example of a mammography exam data-form suitable for use with embodiments of the invention.

FIG. 6*a* is another example embodiment of a ROI data entry form for use with embodiments of the invention.

FIG. 6*b* is the ROI data entry form of FIG. 6*a* with additional ROI categorizations entered.

FIG. 6*c* depicts two additional exemplary embodiments of ROI data entry forms for use with embodiments of the invention.

FIG. 7 is an example of a form showing the statistical analysis of a ROI.

FIG. 8 is an example of a form showing available images that match statistical analysis of the ROI of FIG. 7.

FIG. 9 is an example of a form showing a patient's exam history.

FIG. 10 is an example embodiment of a report generated according an embodiment of the invention.

FIG. 12 is an example embodiment of a web-based form for use with an embodiment of the invention.

FIG. 14 is an example embodiment of a web-based form for use with an embodiment of the invention.

FIG. 17 is an example embodiment of a ROI viewer depicting an individual image for use with embodiments of this invention.

FIG. 18 is an example of an interpretation work-list form for use with embodiments of the invention.

FIG. 19 is an example of a prior examinations form for use with embodiments of this invention.

FIG. 20 is an example of a mammography exam data-form depicting multiple ROI.

FIG. 21 is an example of a ROI data entry form and an example of a ROI gallery window.

FIG. 22 is an example of a mammogram image with an ROI-seed indicated.

FIG. 23 is an example of a mammogram image with an ROI-boundary indicated.

Figure 1:
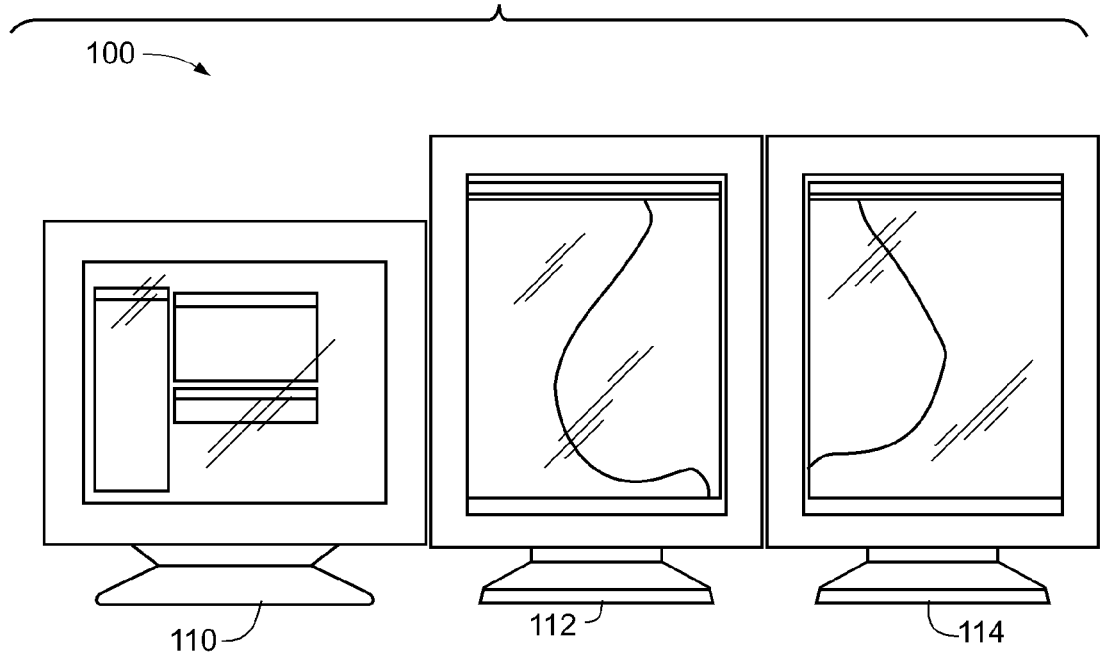
FIG. 1 is an example mammogram information system (MIS) display workstation according an embodiment of the invention.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention as defined by the appended claims.

DETAILED DESCRIPTION OF THE FIGURES

In the following detailed description of the various embodiments of the present invention, numerous specific details are set forth in order to provide a thorough understanding of various embodiments of the present invention. However, one skilled in the art will recognize that the present invention may be practiced without these specific details. In other instances, well-known methods, procedures, and components have not been described in detail so as to not unnecessarily obscure aspects of the various embodiments of the present invention.

This specification includes various embodiments of the present invention describe mammography information systems that may be used for a variety of functions to diagnose tissue abnormalities. These functions include the review, analysis, and categorization of images collected by any of a variety of imaging techniques. While the various embodiments of the present invention is directed to the review of mammogram images, it will be understood that, in some embodiments, that images of tissues depicting other portions of a human or animal anatomy can also be diagnosed with the aid of an embodiment of the present invention. Examples of other such portions include, but are not limited to, cerebral, vascular, thoracic, or other regions that may benefit from medical imaging procedures and review by medial or other properly trained users.

Embodiments provide a computerized mammography information system that allows for the digital correlation of a wide variety patent data related to a mammography image or other breast tissue diagnostic imaging procedures. An exemplary system is able to electronically track breast tissue abnormalities across multiple image types, provide a customizable interface for convenient and efficient image review, allow for an individual user to save preferred image hanging protocols, categorize multiple imaging types, generate statistics, and provide patient correspondence. Additionally, the integration of various computer aided diagnostic/detection (CAD) protocols for multiple image modalities into the system assists the medical professional in reviewing and accurately diagnosing any abnormalities present in a patient's diagnostic images. This advancement in accuracy also provides the benefit of reducing the need for expensive and invasive biopsy or surgery due to false positive diagnosis.

Embodiments of the mammography information system provide an efficient, easy to use, and customizable interface for use by a medical professional for the review and analysis of medical images from a variety of source. The system is capable of integrating medical images acquired through X-ray, CT, ultrasound, MRI, tomosynthesis, or other imaging techniques.

The increasing availability and quantity of digital information representing patient medical data and diagnostic images has created a need for a system that allows a doctor or radiologist to quickly review, organize, and if necessary retrieve, multiple diagnostic images that may be indicative of an individual patient's condition. In addition to the availability of digital mammography images, other patient associated data, such as biopsy or other test results and even entire medical histories or correspondence records can be stored in a digital format. Access to images where the pictured abnormality has been definitively diagnosed can assist with the doctor or radiologist's diagnosis of the new patient's individual condition. Prior to the electronic production, archival, and detailed categorization of patient images, such comparisons were limited to a handful of common abnormalities described in the various medical texts or required laborious manual review of individual patient files.

Therefore, there is a need for a system that will quickly allow a radiologist to select a ROI in a mammogram or other image and correlate the ROI to a mapping or outline of the patient's anatomy in order to improve efficiency of patient diagnosis and record retrieval including a mechanism to "clip" a ROI from any image modality, or form of electronic record, and associating that "clipping" with a specific ROI placement in the patient's record.

Additionally, the availability of this collection of breast tissue images and their associated biopsy results presents an opportunity for statistical analysis of the likelihood that a matching region of interest (ROI) in an individual patient's mammography images is malignant or benign and whether or not a biopsy or further imaging should be ordered. Therefore, there is a need for a system that will quickly allow a radiologist to classify a ROI in a mammogram or other image and correlate the ROI to a large pool of existing data samples that have been definitively diagnosed in order to improve the accuracy and efficiency of patient diagnosis. The radiologist can be assisted in the classification of the ROI by a CAD module by automatically detecting potential ROI abnormalities or simply reducing the number of physical or verbal actions needed by the radiologist to enter the ROI classifying data.

In an example embodiment, a MIS is provided for use by a radiologist or other medical professional that preloads all of an individual patient's medical images for a specific portion of the patient's anatomy, regardless of the modality used to create the images. For example, in a breast cancer screening, any available x-ray, ultrasound, MRI, biopsy, or other images for the patient are retrieved and preprocessed by an appropriate CAD algorithm. A CAD module for the appropriate image type can isolate one or more ROI for review in an individual image. The disclosed invention takes these individual CAD results and correlates any common ROI findings between images of the same or different modalities. A summary "map" or outline of the examined patient's anatomy is then generated and displayed for the medical professional along with any other details about the potential ROI(s) that were generated by the CAD module(s).

The mammography image gallery and clipping system according to the present invention provides a convenient organization of all of the images associated with a ROI, regardless of modality, for presentation to a medical professional. The system stores lower resolution clippings, or thumbnail images, for pathological images, reports, and abnormalities found, and optionally categorized, by radiologists or CAD products at a facility that have been entered into a mammography information system. The system stores low resolution images as well as the reference to the original image and ROI of the original image. As more patients are definitively diagnosed and their pathology records updated in the system, the larger the collection of abnormality images depicting a previously diagnosed and imaged condition that become available in the system. This system can be integrated into an existing MIS or utilized as a standalone interface providing access to a large sample of mammogram abnormality images.

The system also provides an efficient mechanism for creating a comprehensive collection of abnormality data. The collection comprising a uniform lexicon of classifications that allows for further analysis and study of the data while still maintaining patient privacy as required by the applicable law. Those skilled in the art of developing and maintaining electronic databases will appreciate and understand the tradeoffs associated with the storage requirements necessary for the implementation of the contemplated system. As numerous mammography facilities implement this non-patient identifying (and HIPAA compliant) data can be transferred to a central location accumulating a more complete database of abnormality images and the corresponding characterization of data points for various pathology types.

In an example embodiment, the method of analyzing and retrieving abnormality tracking data provides a report of the statistical frequency of diagnosed patients both locally and nationally with mammogram ROI classifications similar to an individual patient. The abnormality data can include information disclosing the frequency of similar ROI classifications have been biopsied and the number of biopsies that were malignant or benign. The disclosed method of capturing and reporting abnormality tracking data provides a radiologist or other medical professional a tool to assess the likelihood of a ROI being malignant or benign, and whether or not the patient should undergo additional testing. The system then presents these statistics to the radiologist who can then choose to look further into the underlying related data if he or she desires.

The statistical mammography predictive system according to the present invention provides instantly and continually updated outcome statistics to a medical professional. The system utilizes the information and data points for each and every abnormality found by radiologists at a facility that have been entered into a mammography information system. As more patients are definitively diagnosed and their pathology records updated in the system, the greater the chances that an individual patient will have a condition similar to a previously diagnosed and imaged condition. This system can be integrated into an existing MIS or utilized as a standalone interface providing access to a large sample of mammogram abnormality data.

The system also provides an efficient mechanism for creating a comprehensive collection of abnormality data. The collection comprising a uniform lexicon of classifications that allows for further analysis and study of the data while still maintaining patient privacy as required by the applicable law. Only unique copies of each combination of tracing data points must be kept in the system. As duplicate data is accumulated the counters of the abnormality and its diagnosis as benign or malignant are incremented. This aggregation of data creates a compact and anonymous abnormality database for the medical location. If desired, a complete reference of all abnormality data can be maintained. Those skilled in the art of developing and maintaining electronic databases will appreciate and understand the tradeoffs associated with the storage requirements necessary for the implementation of the contemplated system.

As numerous mammography facilities implement this non-patient identifying (and HIPAA compliant) data can be transferred to a central location accumulating an more complete database of abnormalities and the corresponding benign or malignant counters for each combination of tracking points and pathology. Therefore, the large number of recorded abnormalities can be culled down to a manageable set of unique combinations specified by radiologists around the country. This culling, or grouping of duplicate abnormalities, allows for a medical professional to access a comprehensive database of the known set of abnormalities nearly instantaneously.

In a further embodiment, the system disclosed provides a mechanism to evaluate, validate, and improve any of a variety of existing CAD modules and techniques by providing an efficient platform for testing the cad module or technique against a wide variety of known, physician evaluated, and definitively diagnosed, patient abnormalities or ROI.

The invention can be better understood by reference to FIGS. 1-19. FIG. 1 illustrates an example embodiment of a mammogram display workstation 100. A typical mammogram display workstation 100 includes a controller display system 110 and at least one high-resolution image monitor 112. One or more additional high-resolution image monitor units 114 can also be used to provide additional viewing area to provide for the comparison of two or more images at full resolution. The controller display system 110 is any of a variety of commonly available video display monitors coupled to a personal computer such as an IBM-PC or compatible system running a version of the Microsoft WINDOWS operating system, or the equivalent thereof. In an embodiment, the image monitors 112 and 114 are liquid crystal displays (LCDs) that provide high-resolution and enhanced contrast for ease of viewing images, but may also be a cathode ray tube or other appropriate display in other embodiments. An exemplary image monitor can display approximately 2500×2000 pixels, although a variety of image monitor sizes are contemplated. In one embodiment, the mammogram display workstation 100 includes a server computer (not shown) that runs DICOM communications components of the mammogram display workstation 100; alternatively, this DICOM software may run on the controller display system 110. In yet another embodiment, a server computer is included that runs an Archived Image Retrieval service; alternatively, this software may also run on the controller display system 110 or on the DICOM compliant server.

The mammogram display workstation 100 includes software that allows images to be analyzed using the image processor in the controller display system 110 to analyze each image of a study set, compare with complementary images to generate a suspect list to reduce false indicators, and to generate graphic overlay images to identify areas of interest. When an image is displayed on an image monitor 112 or 114, imaging tools included in the system allow a user working with the system to further manipulate an image. These software tools may provide magnification of a desired region of an image; image inversion, reversal, rotation, or other repositioning; image/background color inversion; noise filtering from images to reduce or eliminate extraneous data and enhance pertinent image data; customized side-by-side image comparisons; and image reorganization, for example.

Figure 2:
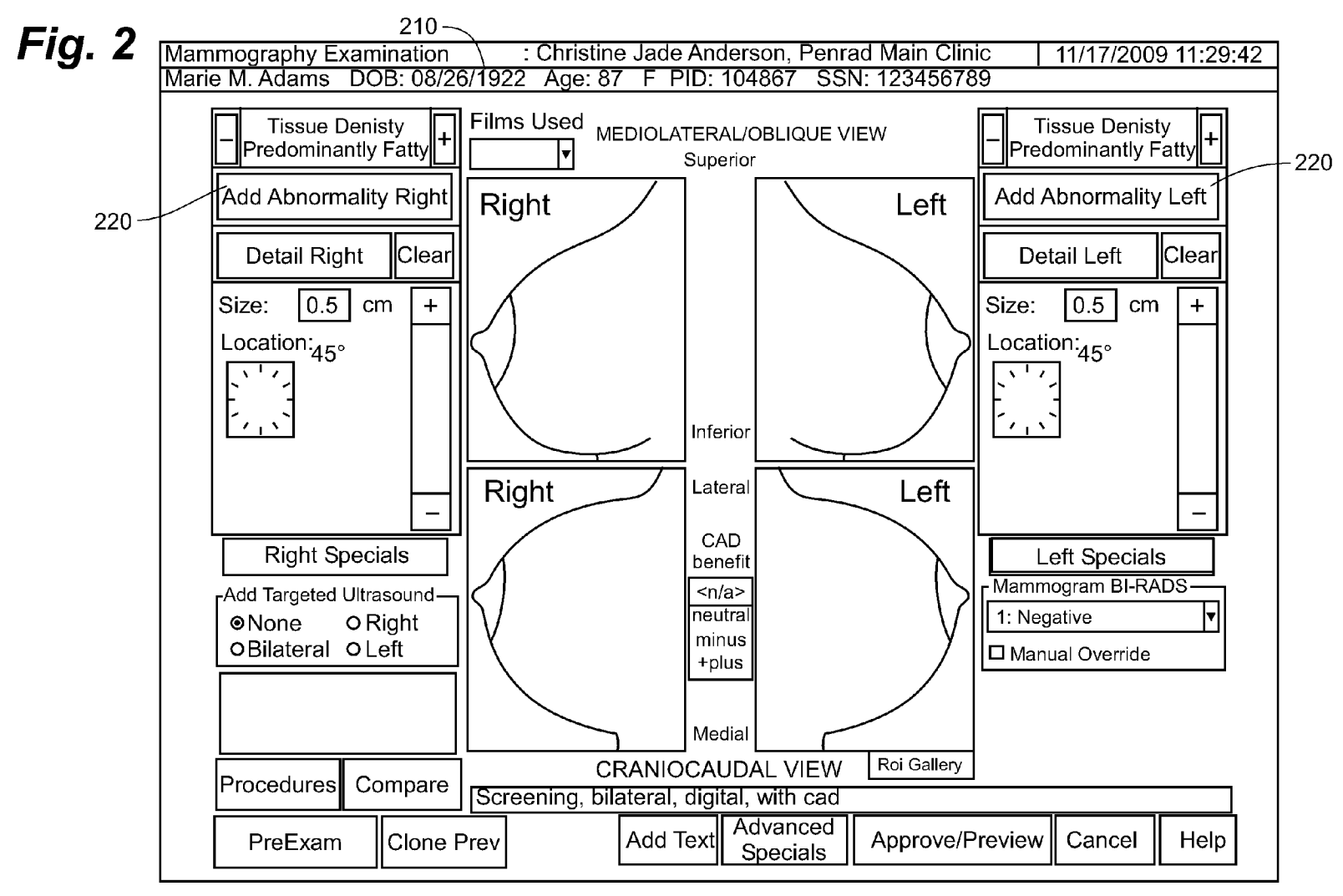

FIG. 2 illustrates an example embodiment of a medical diagnostic system that includes an abnormality-summary window 200. Abnormality-summary window 200 provides a convenient patient information summary 210 and an interface to import or enter additional data. In window 200 the radiologist can enter abnormality data for either the left or right breast by clicking on an "Add Abnormality" button 220. Additionally, a user can import a CAD report detailing any abnormalities that have been detected by existing CAD software. Examples of suitable CAD software include the CadStream product by Confirma and the B-CAD product by Medipattern, among others.

Figure 3:
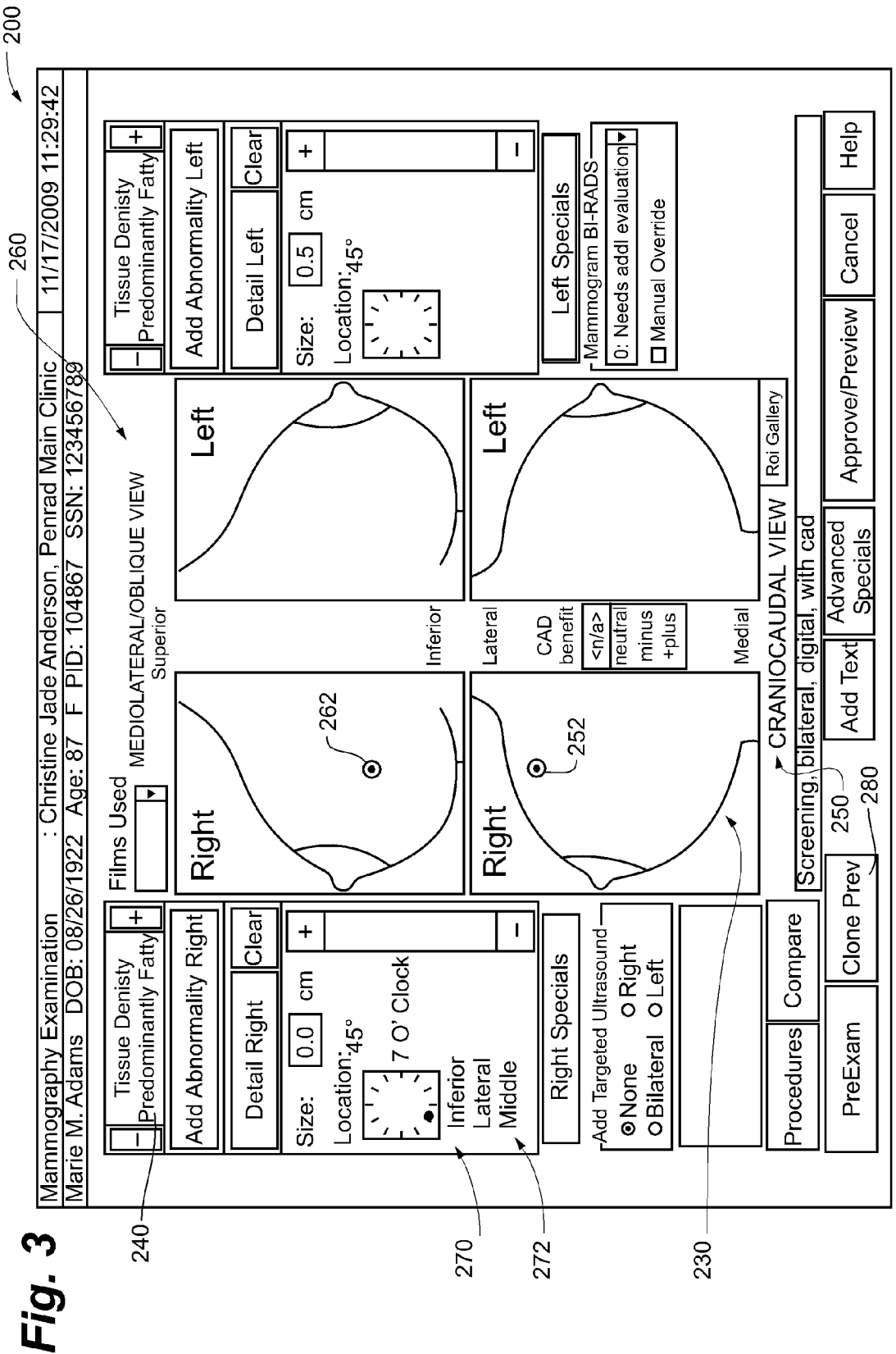
FIG. 3 is an example of the mammography exam data-form of FIG. 2 indicating a region of interest (ROI).

As shown in FIG. 3, imported CAD information stored in compliance with a pre-determined system such as BI-RADS can be used to generate a wire-frame map or guide 230 depicting the location and depth of a ROI in or on a patient's anatomy that was detected by the CAD software or entered manually by a radiologist. The density of the patient's tissue is also presented in selector 240. The guide 230 includes both a craniocaudal (CC) view 250 and a mediolateral/oblique (ML) view 260 of both the left and right breasts of a patient. The ROI is depicted by the craniocaudal mark 252 and the mediolateral mark 262. In other situations, an abnormality may only be visible in one or the other of the ML or the CC view and, accordingly, only a single mark would be displayed in either the craniocaudal (CC) view 250 or the mediolateral/oblique (ML) view 260.

In an embodiment, the ROI data underlying either craniocaudal mark 252 or mediolateral mark 262 can be represented as the number of pixel spaces from at least two edges of the original image represented by the ROI. The retention of the number of pixels from at least two edges provides for the derivation of the location of the ROI on the original image. This allows the storage of multiple ROI for a single high-resolution image without the need to store multiple copies of the high-resolution image or even high-resolution clippings. It also permits derivation or mapping of an ROI in one image to other images based on known pixel sizes and edge distances.

In another alternative embodiment, the data underlying these two marks are used to then calculate an approximate location of the abnormality as viewed by a physician when facing the patient. This calculation also compensates for the fact that during the creation of a mammography image, the patient's breast is compressed to increase the amount of viewable tissue in the two-dimensional x-ray image. Additionally, compensation must be made for the angle at which the mediolateral/oblique view 260 is taken relative to the craniocaudal view 250 during mammogram imaging. Those skilled in the art will appreciate that the two views are not necessarily created at angles exactly perpendicular to each other due to the wide variety of patient anatomy and the need to capture as much tissue as possible in each image. The breast orientation, size and thickness information is provided along with the mammogram image. The resulting combination of the craniocaudal data and the mediolateral data produce the clock-position 270 as shown for the exemplary ROI. This calculation is not calculated if the ROI is only visible on a single image, as both a craniocaudal and mediolateral position are required, along with a distance either from the patient's nipple or chest wall, to calculate the location of the ROI in three-dimensional space.

An abnormality does not need to be located or observable in both views to be characterized. Often in mammography an abnormality is only seen in one view and additional imaging is conducted to confirm its location in another view. The additional imaging can also reveal superimposed tissue, a situation in which the breast tissue of several layers was compressed together causing a potential mass seen in a single image with the appearance of an actual abnormality. A radiologist viewing multiple images of the same tissue area can appropriately categorize these situations.

Also shown in FIG. 3 is a three-word indication 272 of the approximate location of the ROI in the patient's breast. In this example the ROI is located in the inferior (lower), lateral (outside), middle (distance between the chest and nipple) portion of the patient's right breast. Similar terms for the remaining quadrants and depth are provided by the ACR guidelines and will be understood by those skilled in the art.

An additional feature of the system is the capability of importing any ROI from a patient's previous examination that are already present in the system's database. A radiologist or technician can select the "Clone Prev" button 280 to review and import data from a previous examination. This feature further eliminates the need for duplicated effort on the part of the medical professional conducting the review of the patient's exam images.

Figure 4:
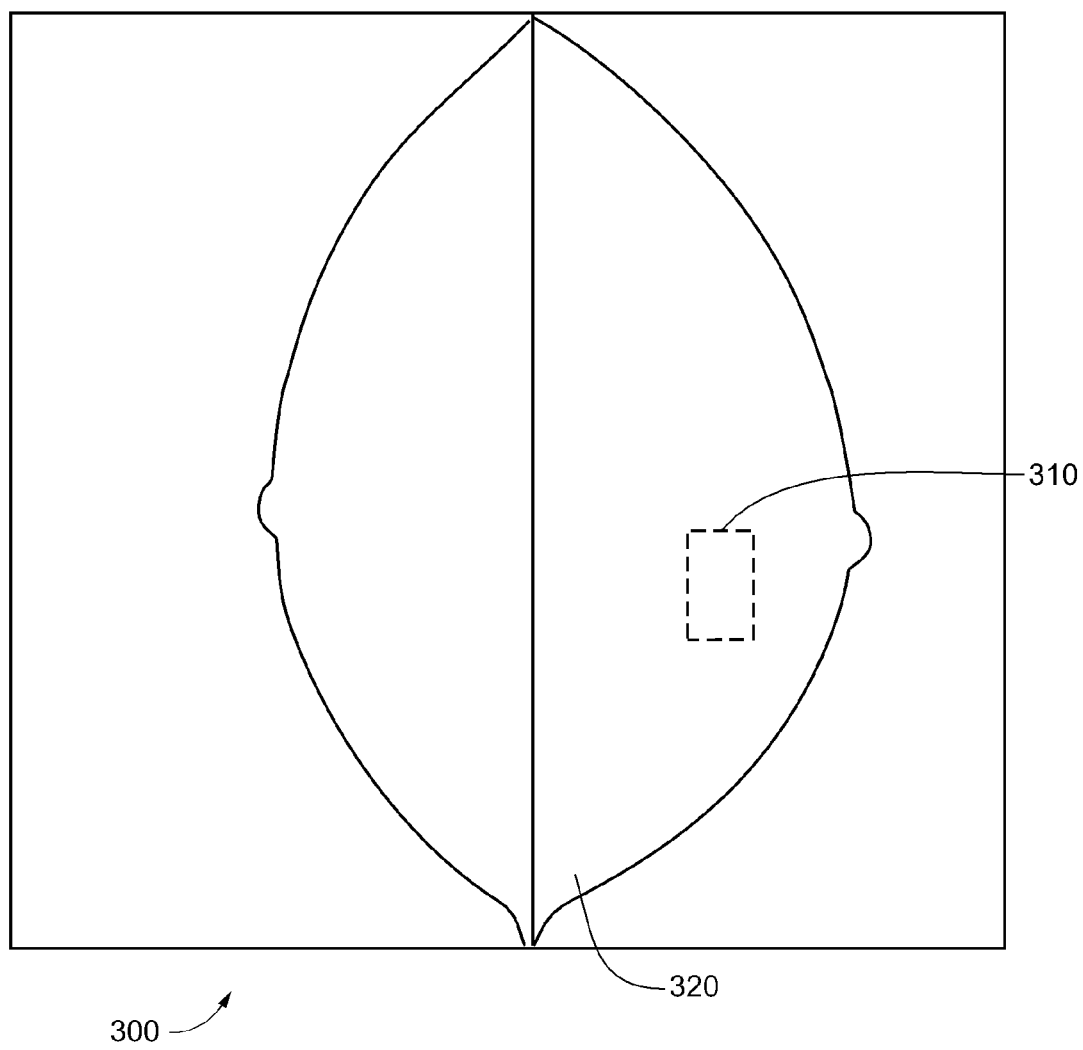
FIG. 4 is an example of a mammogram image with an ROI indicated.
Figure 5:
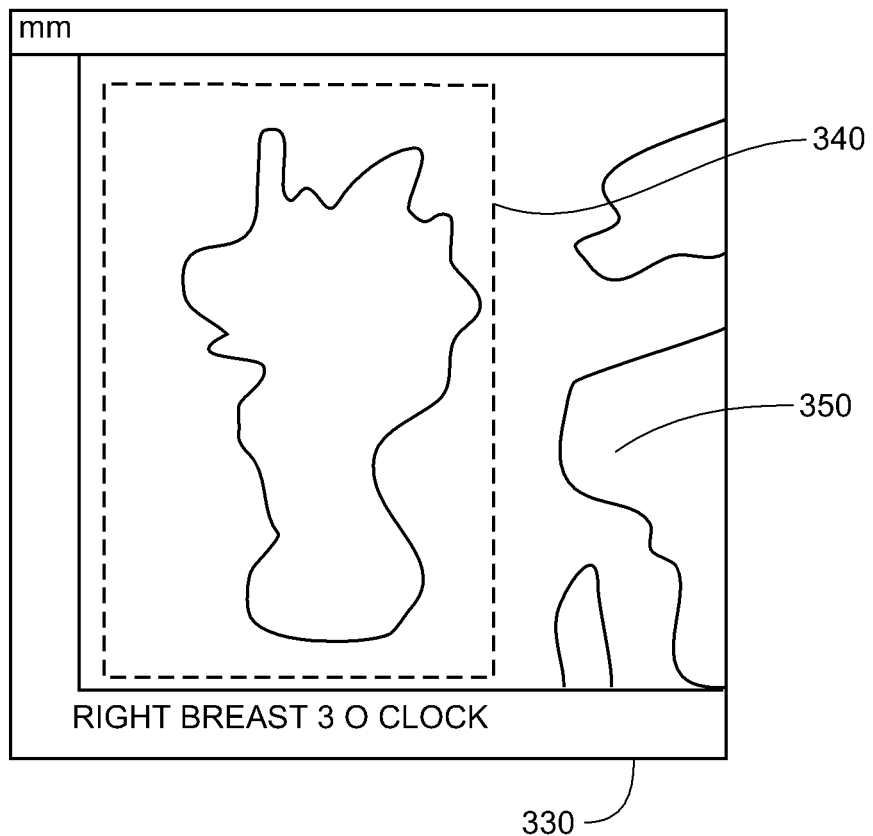
FIG. 5 is an example of an ultrasound image with an ROI indicated.

The system is capable of handling a variety of imaging technologies. FIG. 4 depicts an exemplary x-ray generated mammogram image 300 with an ROI indicated by a dashed outline 310 on the image 300 of the patient's breast tissue 320. FIG. 5 depicts an exemplary ultrasound image 330 with an ROI indicated by a dashed outline 340 on the image 330 of the patient's breast tissue 350. While the type of information depicted in a mammogram image 300 is clearly different from the ultrasound image 330, the system maintains the ROI indicated on each respective image by storing the coordinates of each ROI as an offset, in one embodiment utilizing the number of pixels, from at least two edges of the original digital image, regardless of the technique employed to generate the image. These coordinates are then used to calculate the distance from the patient's chest wall, nipple, or other appropriate reference point, to determine the measurements defining the location of the ROI. Similar techniques can be applied to other imaging technologies such as MRI or CT images that are capable of being stored in a standardized digital format where the correlation of the number of pixels in the image to the real-world distance depicted in the image is known.

FIG. 6a depicts an embodiment of an abnormality-detailing window 400. The detailing window 400 provides an interface for a radiologist to enter or view the detailed attributes that describe an abnormality in a selected ROI. FIG. 6a depicts the single attribute 402 of a "Mass" as being selected to describe the ROI depicted in FIG. 3. As indicated by the system, the presence of a mass alone is generally not enough to indicate the presence of a malignancy. The radiologist then selects an impression 404 and an appropriate recommendation in the "Impression & Recs" area 406. In one embodiment, the system suggests an impression or recommendation in area 406 based on other selected attributes in window 400, which can then be reviewed by the radiologist and altered, if desired. The system can also dynamically and automatically adjust the selection in area 406 if other attributes in window 400 are changed during review. In other embodiments, area 406 is selectable by a radiologist or doctor.

The abnormality-detailing window 400 can include a profiler button 410 that provides a count of matching abnormalities and their pathological outcome. The profiler button 410, or another appropriate window, displays the number of biopsies performed that were diagnosed as malignancies 412, the number of biopsies performed that were diagnosed as benign 414, and the total number of matching abnormalities 416 in the database. The sum of the number of malignancies 412 and the number of benign 414 is the total number of biopsies performed on abnormalities possessing the same attributes selected in detailing window 400 at that location. The second line 418 of profiler window 410 displays these same quantities found in a national database. As discussed above, the single attribute of a Mass 402 in FIG. 6a yields a relatively low number of malignancies 412 (roughly 1.4%) of similar abnormalities in the local database. The combination of the number of malignancies 412 and the number of benign 414 is also a low percentage of the total number of similar abnormalities, indicating a low frequency of requests by the patient's physician for a biopsy. The profiler button 410 is depicted in the lower corner of the screen to provide a convenient, yet out of the way area to present statistical information. Other locations or embodiments, such as a floating window that can be repositioned by the radiologist are contemplated.

Two database versions are typically present in every system—one is the "local" version containing the data specific to the medical facility where the system is installed. This local data can be subsequently uploaded to a centralized server to be integrated with into a "regional," "national," or "global" version of the database. This allows individual users to compare their own facility's results with a larger sample of results. Additionally, the "local" version can be linked to the on-site examination image data, allowing the radiologist to see other examinations related to a specific pathology finding or set of characteristics. The radiologist can then nearly instantly view selected examinations, images, or specified regions of interest retrieved from the local database. The system can also be configured to link to information and retrieve images from the larger databases, although in one embodiment this can be done without any patient identifying information.

FIG. 6b depicts the abnormality-detailing window 400 of FIG. 6a, with three additional characteristics that describe the ROI. The Mass 402 is characterized as "Irregular" 420, "Microlobulated" 422, and having a "High density" 424. In the "Impression & Recs" area 406 the addition of the "5 Highly suggestive" 426 attribute indicates that a follow-up examination of the patient is necessary. In this case, the radiologist has selected the "Ultrasound guided bx" option 428, indicating that the recommended next step for the patient is an ultrasound-guided biopsy of the abnormality.

The addition of the three ROI characteristics in FIG. 6b significantly narrowed the number of matching abnormalities in the MIS database as shown in the profiler button 410. While only half of the biopsied abnormalities resulted in a result of malignancy 412 for the local database, as seen in the national database line 418, the vast majority of biopsied abnormalities of this type were malignant. While the relatively low number of data points presented for this abnormality type may not be sufficient to draw any definitive conclusions, this example shows the utility of being able to compare a local sample with a larger multi-site database of abnormalities providing an indication to the local medical personnel that further review of this abnormality scenario may be required. Those skilled in the medical and radiology arts will appreciate these and other advantages that this collection of data and the ease of access provided by the system yield.

Figure 6C:
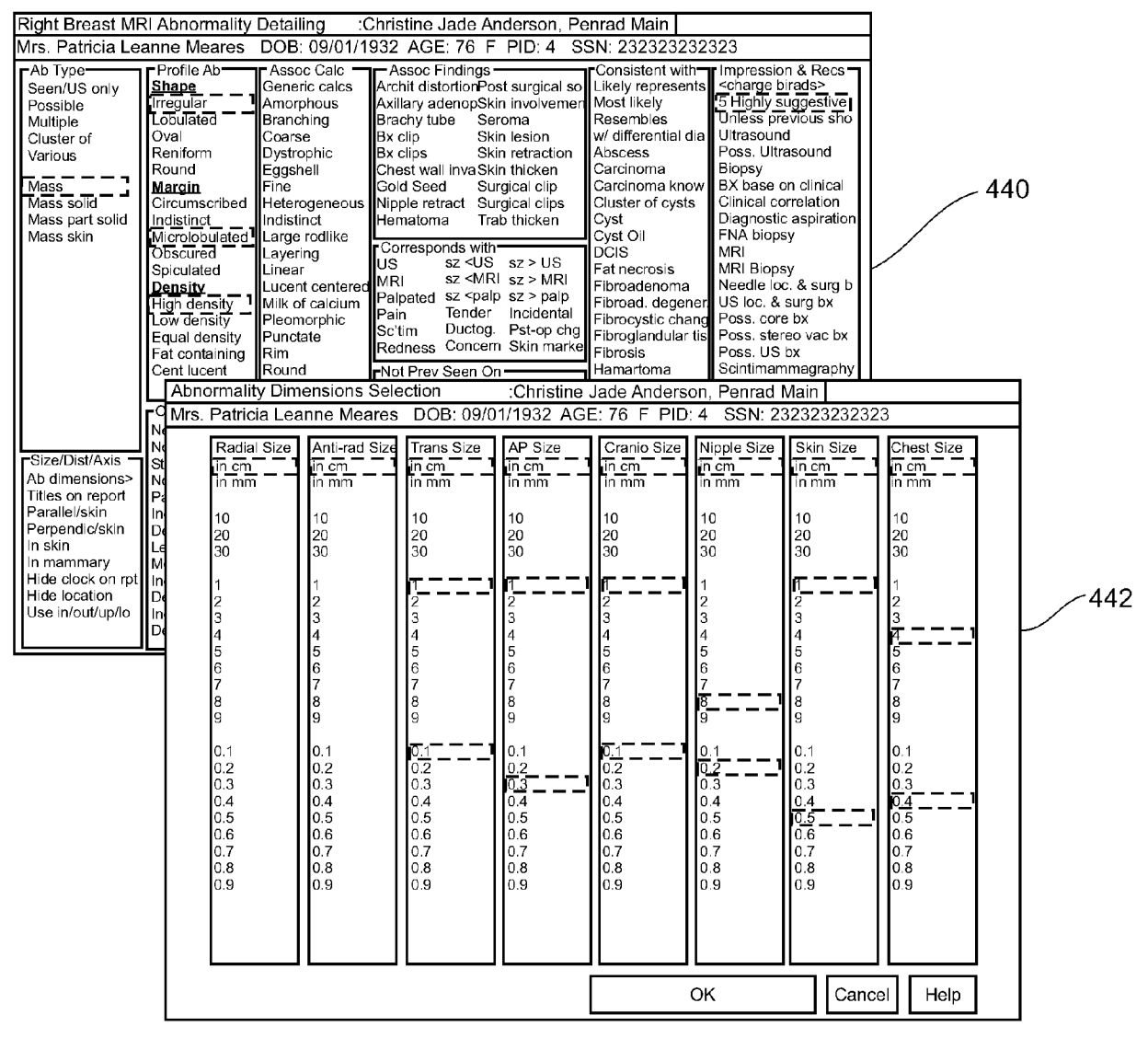

FIG. 6c depicts another example of a right breast MRI abnormality-detailing window 440 and an example of an MRI abnormality-dimensioning window 442. These two windows display the BI-RADS compatible data points, optionally generated by a CAD software package used to pre-evaluate and generate the ROI in the MIS. In one embodiment, the CAD software package can populate the various fields presented by an abnormality window, such as exemplary MRI abnormality-dimensioning window 442. These windows also provide a radiologist with an interface to adjust, re-characterize, correct, or remove the ROI data based on their professional assessment of the ROI depicted in the patient's images. As depicted, in abnormality-dimensions window 442 a radiologist can quickly select or change the radial size, anti-radial size, transverse size, AP size, cranio size, distance from the nipple, distance from the skin, and distance from the chest, of the abnormality. Other appropriate measurements or mechanisms for entering these values are also contemplated.

The system contemplated in the example embodiment dynamically updates the values shown in the profiler button 410, of FIG. 6b, every time a new attribute is selected in abnormality-detailing window 400. One embodiment can achieve this high access speed by assigning an enhanced version of ACR lexicon descriptors to individual bits in a group of integers. This approach also yields a relatively compact database size, further minimizing search time. The tables below provide an exemplary sampling of potential abnormality lexicons. Each item in a lexicon is assigned a value. In Table 1, the STATS_VALUES field first provides a specified index into a list of database field values. These database fields are assigned indexes numbered 0 to n−1. The second hexadecimal value is the actual value assigned to the individual lexicon item. When this item is selected during an examination, the specified bit value is set in the assigned integer field using a bitwise OR operation. The LISTBOX_NAME column provides the general description of where on the abnormality-detailing window 440 the attribute would be grouped. The ITEM_NAME column provides the detailed characteristic that a radiologist can select when characterizing a patent image.

TABLE 1

Mammogram Lexicon Item Detailing

| LISTBOX_NAME | ITEM_NAME | STATS_VALUES |
| --- | --- | --- |
| Specify Abnormality | Fibrocystic tissue | 0.0 × 00000001 |
| Specify Abnormality | Cyst simple | 0.0 × 00000002 |
| Specify Abnormality | Mastitis area | 0.0 × 00000004 |
| Specify Abnormality | Mass solid | 0.0 × 00000008 |
| Specify Abnormality | Lesion | 0.0 × 00000010 |
| Specify Abnormality | Cyst | 0.0 × 00000020 |
| Specify Abnormality | Abscess | 0.0 × 00000040 |
| Specify Abnormality | Mass | 0.0 × 00000080 |
| Specify Abnormality | Papillary lesion | 0. × 000000100 |
| Profile Abnormality | Irregular | 1.0 × 00000001 |
| Profile Abnormality | Lobulated | 1.0 × 00000002 |
| Profile Abnormality | Oval | 1.0 × 00000004 |
| Profile Abnormality | Reniform | 1.0 × 00000008 |
| Profile Abnormality | Round | 1.0 × 00000010 |
| Profile Abnormality | Circumscribed | 1.0 × 00000020 |
| Profile Abnormality | Microlobulated | 1.0 × 00000040 |
| Profile Abnormality | Obscured | 1.0 × 00000080 |
| Profile Abnormality | Indistinct | 1.0 × 00000100 |

TABLE 1-continued

Mammogram Lexicon Item Detailing

| LISTBOX_NAME | ITEM_NAME | STATS_VALUES |
|---|---|---|
| Profile Abnormality | Spiculated | 1.0 × 00000200 |
| Profile Abnormality | Intraductal | 1.0 × 00000400 |
| Profile Abnormality | Irregular | 1.0 × 00000800 |
| Profile Abnormality | Smooth | 1.0 × 00001000 |
| Profile Abnormality | High density | 1.0 × 00002000 |
| Profile Abnormality | Equal density | 1.0 × 00004000 |
| Size and Distance | Parallel/skin | 1.0 × 00800000 |
| Size and Distance | Perpendic/skin | 1.0 × 01000000 |
| Assoc Calcs | Generic calcs | 2.0 × 00000001 |
| Assoc Calcs | Amorphous | 2.0 × 00000002 |
| Assoc Calcs | Branching | 2.0 × 00000004 |
| Assoc Calcs | Coarse | 2.0 × 00000008 |
| Assoc Calcs | Dystrophic | 2.0 × 00000010 |
| Assoc Calcs | Eggshell | 2.0 × 00000020 |
| Assoc Calcs | Lucent-centered | 2.0 × 00002000 |
| Assoc Calcs | Milk of calcium | 2.0 × 00004000 |
| Assoc Calcs | Pleomorphic | 2.0 × 00008000 |
| Assoc Calcs | Punctate | 2.0 × 00010000 |
| Assoc Calcs | Rim | 2.0 × 00020000 |
| Assoc Calcs | Round | 2.0 × 00040000 |
| Assoc Calcs | Skin | 2.0 × 00080000 |
| Assoc Calcs | Spherical | 2.0 × 00100000 |
| Assoc Calcs | Suture | 2.0 × 00200000 |
| Assoc Calcs | Vascular | 2.0 × 00400000 |
| Assoc Calcs | Clustered | 2.0 × 00800000 |
| Assoc Calcs | Diffuse | 2.0 × 01000000 |
| Assoc Calcs | Grouped | 2.0 × 02000000 |
| Assoc Calcs | Linear | 2.0 × 04000000 |
| Assoc Calcs | Regional | 2.0 × 08000000 |
| Assoc Calcs | Scattered | 2.0 × 10000000 |
| Assoc Calcs | Segmental | 2.0 × 20000000 |
| Associated findings | Hematoma | 3.0 × 00000001 |
| Associated findings | Nipple retract | 3.0 × 00000002 |
| Associated findings | Seroma | 3.0 × 00000008 |
| Associated findings | Skin involvement | 3.0 × 00000010 |
| Associated findings | Skin lesion | 3.0 × 00000020 |
| Associated findings | Skin retraction | 3.0 × 00000040 |
| Associated findings | Skin thicken | 3.0 × 00000080 |
| Associated findings | Trab thicken | 3.0 × 00000100 |
| Change From Prior | Incr in size | 3.0 × 00000200 |
| Change From Prior | Decr in size | 3.0 × 00000400 |
| Change From Prior | Incr in calcs | 3.0 × 00002000 |
| Change From Prior | Decr in calcs | 3.0 × 00004000 |
| Change From Prior | Incr in number | 3.0 × 00008000 |
| Change From Prior | Decr in number | 3.0 × 00010000 |
| Change From Prior | Less prom. | 3.0 × 00020000 |
| Change From Prior | More prom. | 3.0 × 00040000 |
| Associated findings | Archit distortion | 3.0 × 00080000 |
| Associated findings | Axillary adenop | 3.0 × 00100000 |
| Associated findings | Chest wall invas | 3.0 × 00200000 |

The database of ROIs created from all examinations, detailed abnormalities, and pathology is generated and electronically stored at one or more sites. The information is then concatenated. As each exam and abnormality's result is created using the bitwise technique mentioned above, a search is made for an identical pathology finding with the identical set of bitset integer values (lexicon items) describing the abnormalities. If not found, a single record is created for each final abnormality pathology finding for each unique set of integer "lexicon" values. When duplicates are found, abnormality, benign, and malignant, the appropriate counters are incremented and the data displayed in profiler button 410 is updated.

In querying the database, the user selects lexicon items and/or pathology findings and the statistical system will instantly show "quick" statistics (total #'s only) in profiler button 410 for other exam abnormalities that "include" the profile of selected items. When the radiologist selects "round shape" he will instantly see statistics for all other abnormalities with a "round shape," noting how many were ultimately benign, how many were malignant, and how many were never biopsied. The radiologist can also view a statistical list of findings for all abnormalities with "round shape," perhaps helping determine probabilities for malignancy. If the radiologist subsequently also selects "speculated margin," the same process will occur for all abnormalities with a "round shape" AND a "speculated margin."

An example embodiment can use a bit-setting method to produce a typical database that is small enough such that it can be loaded into the main memory of the MIS to enable rapid retrieval and updates. In an embodiment, the loading process is performed by a background thread during system startup allowing the user to continue working during loading. In querying the database, all the system needs to do is convert the currently selected lexicon items into their corresponding bitmap values, and then search the database using an "exclusive OR" (xor) comparison on the database records. A record matches when all the "set" bit values from the selected items are "set" in the database record being compared. Abnormality, Benign, and Malignant counts on each matching record are tabulated and ultimately presented to the radiologist.

The combination of the high-speed statistical comparison database and the ROI image database allows an embodiment of the system to provide a radiologist with images stored at a local facility for comparative diagnostic purposes. The system also allows a radiologist to select images based on the BI-RADS or other lexicon abnormality descriptors, allowing a comparison of additional images from a larger database or final pathology results if the abnormality was biopsied. Table 2 provides on exemplary mapping of BI-RADS values to the more efficiently stored and searched bit-field values.

TABLE 2

Mammogram Lexicon to BIRADS Conversion and Detailing

| ABNORMALITY | CLASSIFICATION | DESCRIPTOR ID NUMBER | DATABASE BIT-FIELD VALUE |
|---|---|---|---|
| Mass | Irregular | 16 | 0 × 00000001 |
| Shape | Lobulated | 190 | 0 × 00000002 |
| | Oval | 15 | 0 × 00000004 |
| | Reniform | 27 | 0 × 00000008 |
| | Round | 14 | 0 × 00000010 |
| Margin | Circumscribed | 109 | 0 × 00000020 |
| | Microlobulated | 111 | 0 × 00000040 |
| | Obscured | 28 | 0 × 00000080 |
| | Indistinct | 21 | 0 × 00000100 |
| | Spiculated | 29 | 0 × 00000200 |
| | Intraductal | 201 | 0 × 00000400 |
| | Irregular | 20 | 0 × 00000800 |
| | Smooth | 18 | 0 × 00001000 |
| Density | High density | 211 | 0 × 00002000 |
| | Equal density | 213 | 0 × 00004000 |
| | Low density | 212 | 0 × 00008000 |
| | Fat containing | 214 | 0 × 00010000 |
| | Cent lucent | 215 | 0 × 00020000 |
| Wall | Septated internal wall | 25 | 0 × 00080000 |
| | Irregular internal wall | 24 | 0 × 00100000 |
| | Smooth internal wall | 23 | 0 × 00200000 |
| | Thickened wall | 199 | 0 × 00400000 |
| Calcification Type | (generic calcs) | 701 | 0 × 00000001 |
| | Amorphous | 702 | 0 × 00000002 |
| | Branching | 703 | 0 × 00000004 |
| | Coarse | 704 | 0 × 00000008 |
| | Dystrophic | 705 | 0 × 00000010 |
| | Eggshell | 706 | 0 × 00000020 |
| | Fine | 707 | 0 × 00000040 |
| | Heterogeneous | 708 | 0 × 00000100 |
| | Indistinct | 709 | 0 × 00000200 |
| | Large rodlike | 710 | 0 × 00000400 |
| | Layering | 711 | 0 × 00000800 |
| | Linear | 712 | 0 × 00001000 |

TABLE 2-continued

Mammogram Lexicon to BIRADS Conversion and Detailing

| ABNORMALITY | CLASSIFICATION | DESCRIPTOR ID NUMBER | DATABASE BIT-FIELD VALUE |
|---|---|---|---|
| | Lucent-centered | 713 | 0 × 00002000 |
| | Milk of calcium | 714 | 0 × 00004000 |
| | Pleomorphic | 715 | 0 × 00008000 |
| | Punctate | 716 | 0 × 00010000 |
| | Rim | 717 | 0 × 00020000 |
| | Round | 718 | 0 × 00040000 |
| | Skin | 719 | 0 × 00080000 |
| | Spherical | 720 | 0 × 00100000 |
| | Suture | 721 | 0 × 00200000 |
| | Vascular | 722 | 0 × 00400000 |
| Calcification Distribution | Clustered | 751 | 0 × 00800000 |
| | Diffuse | 752 | 0 × 01000000 |
| | Grouped | 753 | 0 × 02000000 |
| | Linear | 754 | 0 × 04000000 |
| | Regional | 755 | 0 × 08000000 |
| | Scattered | 756 | 0 × 10000000 |
| | Segmental | 757 | 0 × 20000000 |
| Foreign body, Scar, or other (typically ignore) | Hematoma | 478 | 0 × 00000001 |
| | Nipple retract | 477 | 0 × 00000002 |
| | Post surgical scar | 479 | 0 × 00000004 |
| | Seroma | 469 | 0 × 00000008 |
| | Skin involvement | 252 | 0 × 00000010 |
| | Skin lesion | 473 | 0 × 00000020 |
| | Skin retraction | 251 | 0 × 00000040 |
| | Skin thicken | 250 | 0 × 00000080 |
| | Trab thicken | 470 | 0 × 00000100 |
| Changes from prior exam | Incr in size | 77 | 0 × 00000200 |
| | Decr in size | 78 | 0 × 00000400 |
| | Incr in calcs | 483 | 0 × 00002000 |
| | Decr in calcs | 484 | 0 × 00004000 |
| | Incr in number (mass) | 481 | 0 × 00008000 |
| | Decr in number (mass) | 482 | 0 × 00010000 |
| | Less prom. | 293 | 0 × 00020000 |
| | More prom. | 294 | 0 × 00040000 |

Detailing window 400 displays information that can be stored as BI-RADS compatible data points, or another suitable lexicon. Optionally the ROI data can be generated by a CAD software package used to pre-evaluate and categorize the ROI in the MIS. Detailing window 400 also provides a radiologist with an interface to adjust, re-characterize, correct, or remove the ROI data based on their professional assessment of the ROI depicted in the patient's images if the radiologist disagrees with the CAD generated results. All of this information can be stored in a database configured to correlate all of a patent's ROI data and images.

The features provided by the system can also be combined with any one of several available computer aided diagnostic (CAD) products to validate, improve, and allow simplified testing of future CAD algorithms. A CAD product can be evaluated by using the electronically compiled descriptions of any abnormalities shown in a collection of ROI images to compare the CAD software algorithms against the real world pathology or biopsy results that were actually performed on the ROIs depicted in the image database.

Once the reliable performance of a CAD algorithm is established it may be used to further assist or confirm radiologist assessments of mammography images from new patients, or to alert the medical staff or radiologists when new or previously unclassified abnormalities are detected. Additionally, the integration of a CAD algorithm and the lexicon abnormality descriptors to generate ROI entries, such as those depicted in FIG. 6b, can pre-select the ROI classifications for each abnormality detected by a CAD product. This combination is especially advantageous as it reduces the number of radiologist provided entries to only corrections to the CAD interpretation of an ROI or any ROI that were not categorized initially by the CAD product. While a handful of mouse clicks or keyboard entries, or similar gestures, may seem trivial, the combined time savings over the high volume of patient images that must be reviewed can yield a substantial savings in time, cost and comfort.

In the example embodiment discussed above, the display of the statistical results in profiler button 410 is automatically updated every time the radiologist enters or changes a data point. In another embodiment, the statistical results display window or profiler button 410 is hidden, or the update suppressed, until the entry of all of the patient's data is complete. This alternative embodiment may be useful as a training tool for educating new radiologists by preventing them from being influenced by the statistical updates as they perform their entry of the data points for a patient.

As shown in FIG. 7, when the user activates, or clicks on, the profiler button 410 of FIG. 6b, a window of matching statistical information 500 is displayed. This window of matching statistical information 500 includes the individual quantity 502 and the percentages 504 for malignant and benign outcomes in a sorted itemized list with both local and national data based on the matching selected abnormality features. Additionally, window 500 also includes the various pathology findings 506, as well as the code for that finding 508, contained in the database.

The example embodiment provides a "show exams" button 510 that allows a radiologist to retrieve the examinations for an individually selected pathology type 512. FIG. 8 depicts an examination list window 550 for the selected pathological type 512. The matching exams displayed in FIG. 8 are only those database records from the local facility database. Any records retrieved from a non-local database would not contain any patient identifying information. The embodiment of the MIS depicted here further provides the radiologist with the opportunity to select a record 560 of individual patient with the same diagnosis 512 for further review. The selection of the "View patient priors" button 570 directs the system to open a window containing the selected patient's examination record and "Send Images to Viewstation" button 572 that can be selected to send images to display workstation 100 or image monitors 112 and 114 that allows the radiologist to view multiple matching imaging features and pathological outcomes in similar imaging modalities.

FIG. 9 depicts an exemplary prior exam window 600 displaying the images for an individual patient's exam. Prior exam window 600 includes existing or historical exam images for the selected patient for referencing process of care. By selecting an individual exam report 602 and then one of the "View Full" 604, "Preview" 606, "Print" 608, or "Send to Viewstation" 610, the radiologist can examine the selected exam report 602 and optionally compare the images contained in that record to the current patient's images. Additionally, the system allows the radiologist to export a variety of bulk data, such as to a CD or other location with the "Create CD" button 612 option. The bulk data may include all of the images related to a single patient or a collection of categorized abnormality images that match a set of selected abnormality attributes or some other data subset.

FIG. 10 depicts a patient report 700 summarizing the details of the CAD or radiologist findings from the examination and analysis of the patient's images. The report 700 can contain a clipped portion of the medical image or a thumbnail picture summarizing the ROI, as well as a multi-perspective wireframe guide that maps the location of the ROI onto the outline of the patient's anatomy.

FIG. 11 through FIG. 14 depict an exemplary embodiment of a standalone or web-based interface 800 to an embodiment of the profiler system. The web-based interface 800 can be accessed with any of the commonly available web browsers such as Microsoft Internet Explorer or Mozilla Firefox. As appreciated by those skilled in the art, a web-based interface may be hosted on a server connected to the Internet for use by a variety of geographically separated individuals or locally where access is limited to a particular facility's local network.

Figure 11:
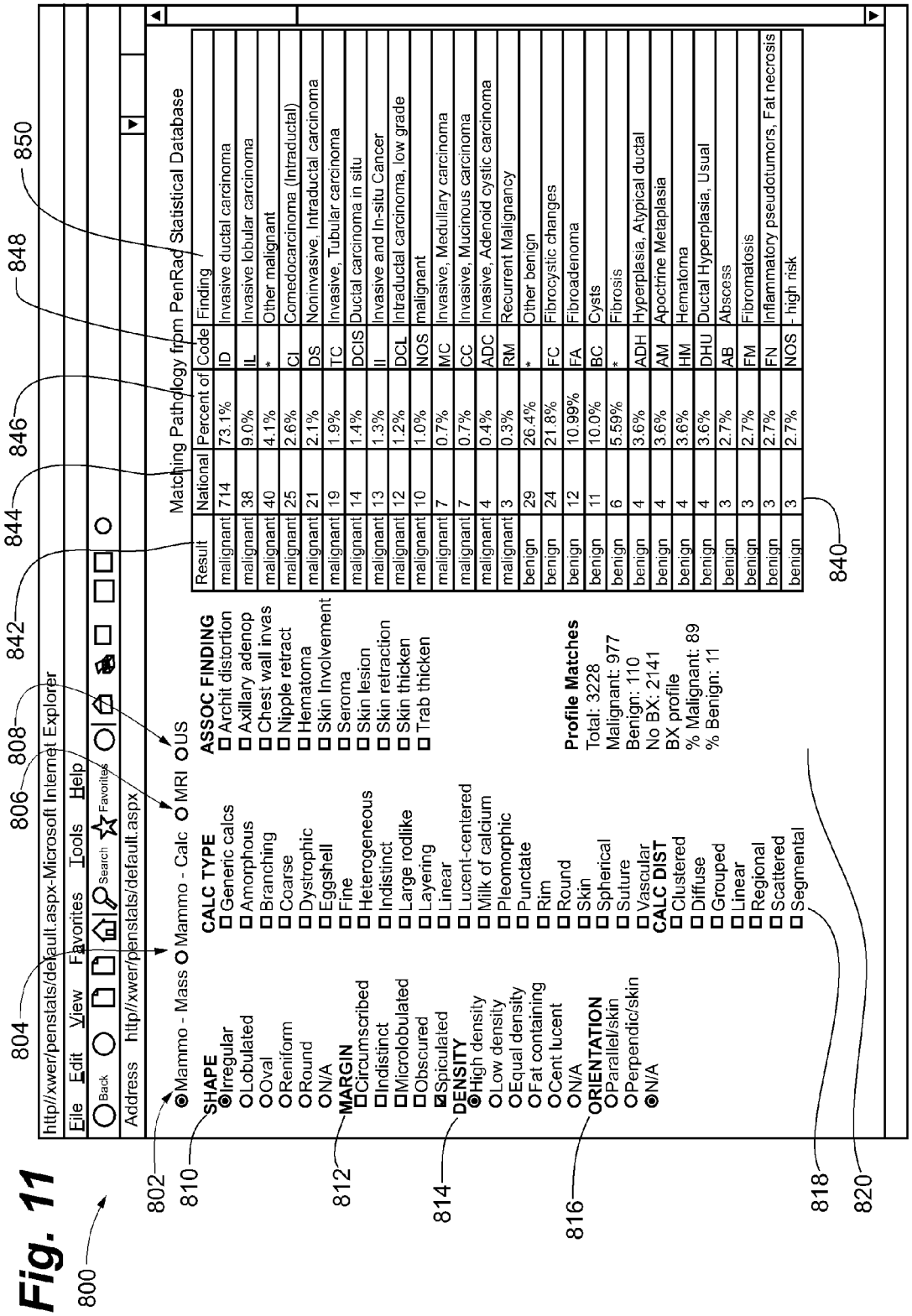
FIG. 11 is an example embodiment of a web-based form for use with an embodiment of the invention.

FIG. 11 depicts a web-based interface 800 providing a mechanism to select various characteristics regarding abnormality information contained in a database. Four modalities are presented, Mammogram—Mass 802, Mammogram—Calcification 804, MRI 806 and Ultrasound (US) 808. Depending on the modality selected, additional characteristics related to the selected modality are displayed to provide further details of the abnormality information request. The example depicted in FIG. 11 indicates a request for abnormality information contained in the database where the abnormality is categorized as a Mammogram—Mass 802, has an irregular shape 810, a speculated margin 812, and a high density 814. Mammogram—Mass 802 can also have associated calcification types 818.

As depicted in FIG. 12, the Mammogram—Calcification 804 modality is selected as the primary abnormality, and the Mass column containing the Shape 810, Margin 812, Density 814, and Orientation 816 categories, shown in FIG. 11, are removed from the interface 800. Interface 800 can include a results summary display area 820 and a matching pathology display area 840. The results summary display area 820, in a manner similar to the profiler button 410 of FIG. 6a, displays a count of matching abnormalities and their pathological outcome that were found in the database, as well as the percentages of the biopsied abnormalities that we either malignant or benign.

The matching pathology display area 840 can include a list of findings that can detail the percentages of a pathology diagnosis for abnormalities that were malignant or benign. The display area 840 example includes the result 842 as either malignant or benign, the number of entries 844 in the national database, the percentage 846 that each pathology represents of either the malignant or benign diagnosis, a pathology code 848 and a summary of the finding 850. Both the results summary display area 820 and the matching pathology display area 840 are updated whenever a new abnormality categorization is selected.

Figure 13:
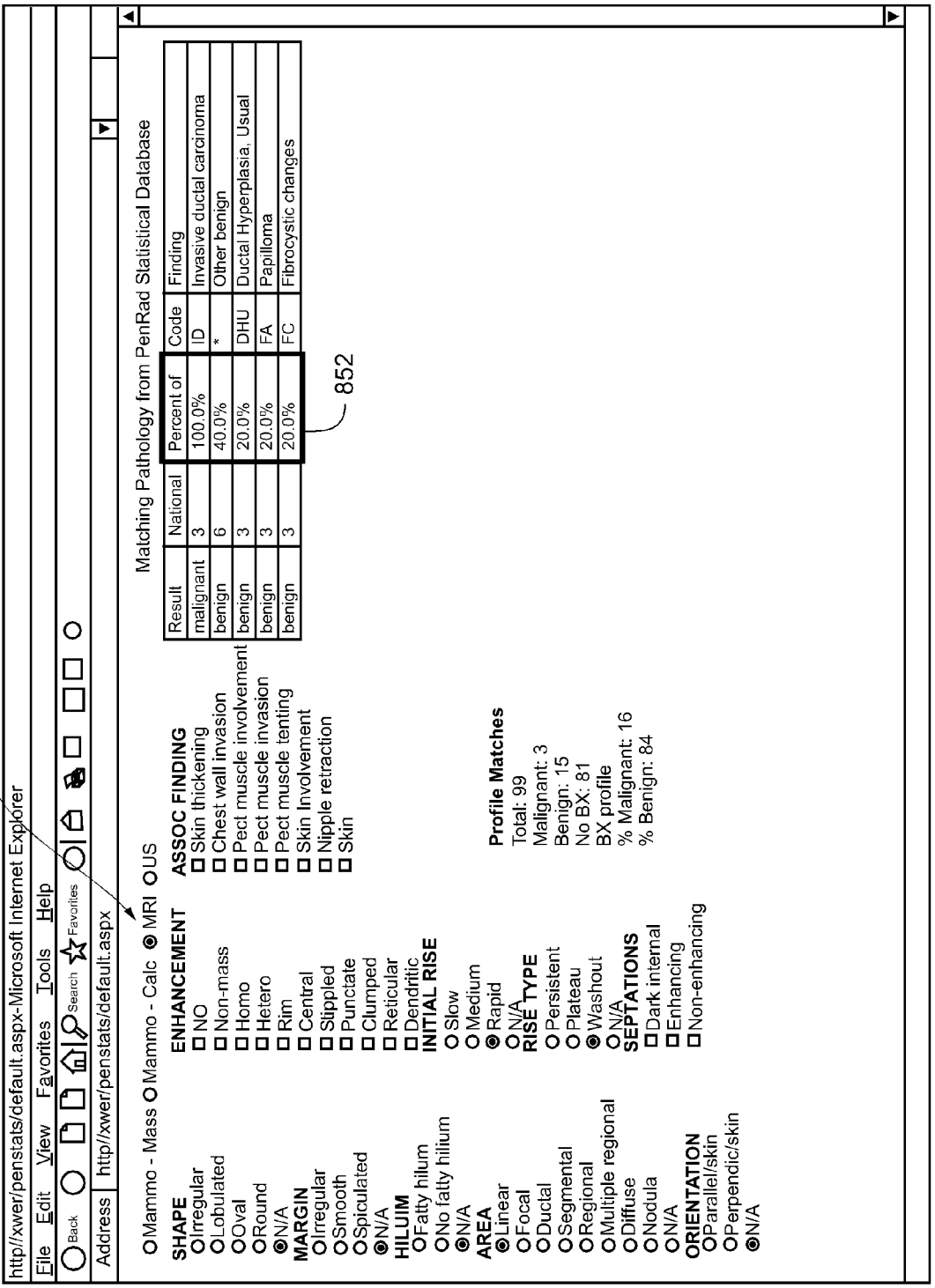
FIG. 13 is an example embodiment of a web-based form for use with an embodiment of the invention.

FIG. 13 depicts an example embodiment of interface 800 displaying categories that are related to the MRI 806 modality. As shown in the "Percent of" column 852 of the matching pathology display area 840, the percentages of the abnormality diagnosis are calculated as the number of relevant diagnosis from the total number of just the malignant or just the benign results. As shown, the percentages of malignant diagnosis equal 100% and the benign diagnosis equal 100%.

FIG. 14 depicts an example embodiment of interface 800 displaying categories that are related to the ultrasound 808 modality. The ultrasound 808 modality includes fields for "Boundary," "Hilum," "Echo," and "Internal Echo" in column 860 that are specific to ultrasound imaging techniques. It is contemplated that other fields, columns, or modalities can be added or presented as needed to accommodate the preferences of the user or to incorporate other new or existing diagnostic technologies.

Figure 15:
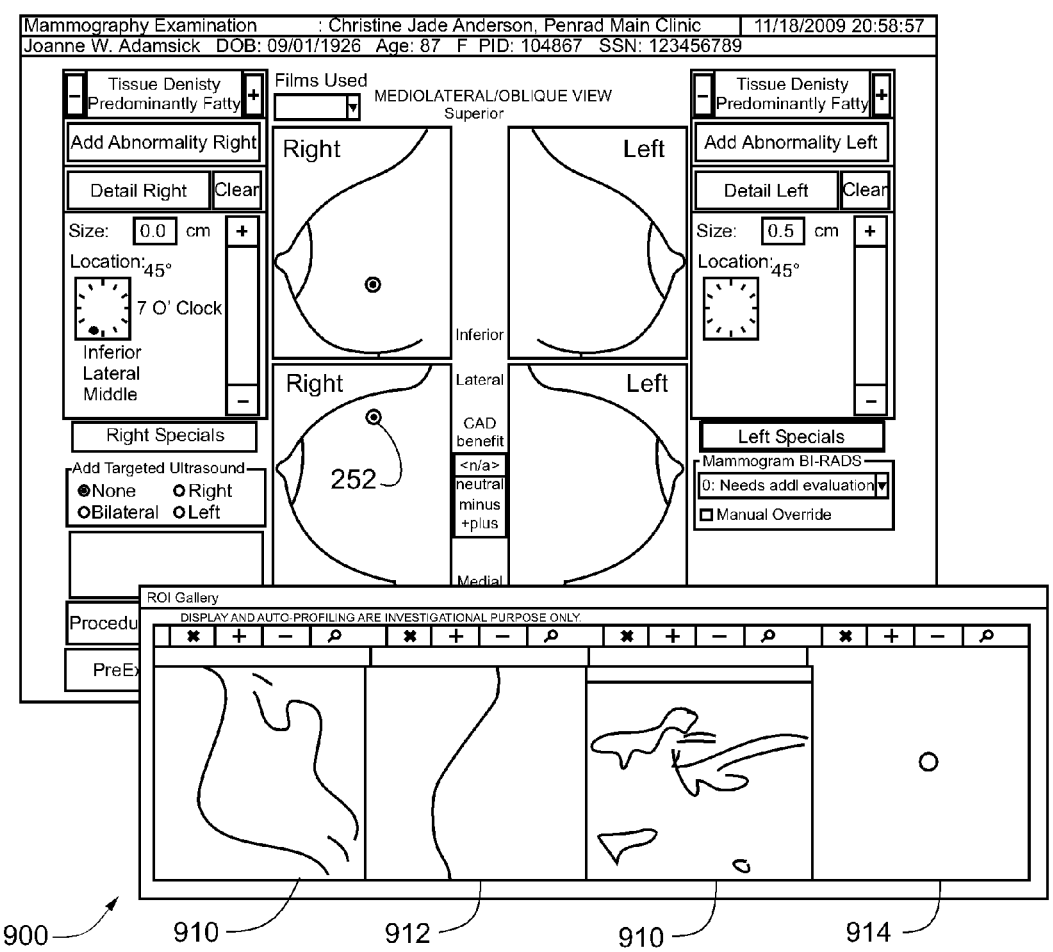
FIG. 15 is an example of a mammography exam data-form and an example of a ROI gallery window.

FIG. 15 depicts an embodiment of a ROI Gallery 900 containing selected image clippings 910 that have been associated with the ROI depicted by the craniocaudal mark 252. The activation of the "Roi Gallery" button 290, shown in FIG. 3, causes the ROI Gallery 900 to be presented to the user. The image clippings 910 can be selected from any region of a medical image available to the radiologist on the MIS. A low magnification image 912 can be useful to identify a large area of tissue. Alternatively, a smaller, higher magnification image 914 can provide the radiologist with greater detail.

The association of image clippings 910 can allow the radiologist to associate a variety of images with the set of categories, such as those associated with the ROI of FIG. 3. By correlating a subset of a full resolution image the radiologist is able to focus on the specific area that is described by the characteristics. This correlation of ROI characteristics with any of a variety of radiologist selected image clippings 910 can then be used in during future examinations to quickly focus in on individual areas that may need review. One example would be clipping a view of an abnormality that the radiologist recommended be reviewed after six or twelve months for any changes in size or appearance.

Additionally, the system provides for the clipping of various modalities of images. In addition to the mammogram images as shown in the ROI Gallery 900, additional images such as ultrasound or MRI captures can also be included in the gallery. One embodiment of this system can employ the storage of individual image clippings 910 in a compressed image format, such as the JPEG image format established by the Joint Photographic Experts Group, or another appropriate standard. The use of a compressed image format provides an acceptable resolution for a thumbnail image for an initial investigation, while requiring less storage space than a high-resolution image format, such as the DICOM format. The system also provides a link from the compressed image clippings 910 to the full-sized high-resolution image for the situations, such as making a diagnostic assessment, that require a radiologist to view the high-resolution image.

In one embodiment of the system, a database of thumbnail or clipped images can provide a source of investigational data that may assist a radiologist in categorizing an abnormality that he or she is unfamiliar with, or for use as a training tool. The association of the ROI categorizations with the clipped images also provides an efficient mechanism to search for individual image clippings 910 of a particular type of abnormality or to provide a convenient link to pathology reports or patient correspondence. Non-image based information such as patient correspondence or reports can be stored in the ROI Gallery 500 either in their native format or in an image format, such as JPEG, TIFF, GIF, or another appropriate standard, derived from a screen-capture of the report or document.

Figure 16A:
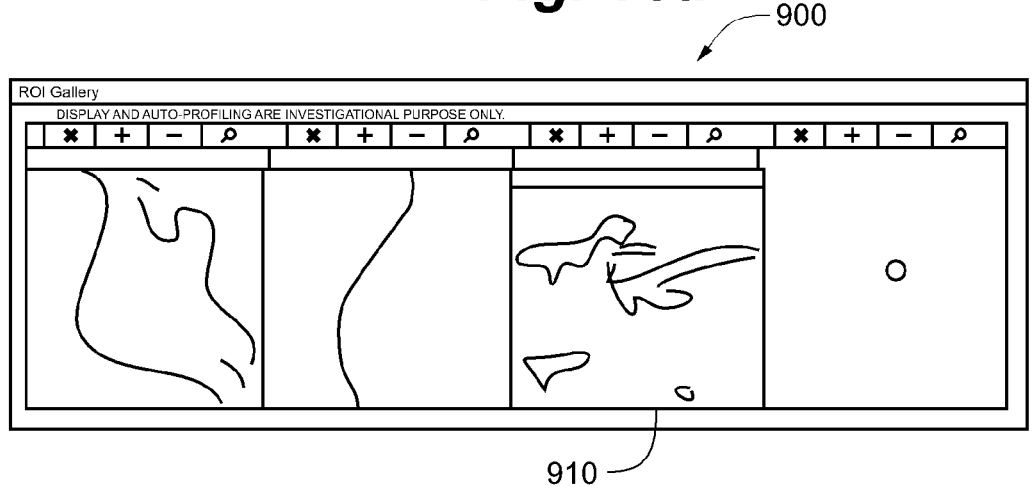
FIG. 16a is an another depiction of the ROI gallery window of FIG. 15.
Figure 16B:
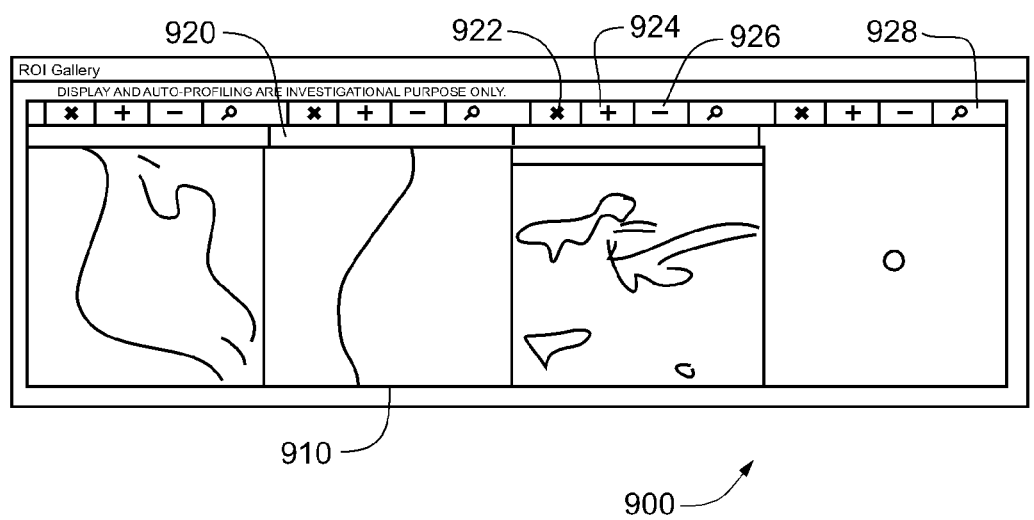
FIG. 16b is another example of a ROI gallery window for use with embodiments of this invention.

FIG. 16a is another depiction of ROI Gallery 900. Image clipping 910, as well as other images, can be attached or associated directly to an abnormality, such as ROI, depicted by the craniocaudal mark 252. FIG. 16b depicts of ROI Gallery 900 with a single highlighted image clipping 910 as indicated by highlight-bar 920. Various exemplary tools are shown in ROI Gallery 900 that provide for the manipulation of individual image clippings. When an image is associated to an abnormality, the title bar 920 changes color, indicating a direct association. Tapping the "+" 924 provides a mechanism to attach image to abnormality 910. Tapping "−" 926 disassociates image clipping 910 if attached to an ROI. A double-click on image clipping 910 or tapping on magnification button 928 brings up an individual ROI viewer 950 to allow a large view along with access to other imaging tools.

Within the title bar the description of the view is displayed from the image it was obtained from, for example RCC (RightCranioCaudal) image. In an embodiment, if the image was processed through a CAD tool, the feature descriptors, such as CAD-generated ROI outlines provided by that tool, are displayed. In another embodiment, feature descriptors can be superimposed as an overlay on top of the image. Alternatively, a hovering tool bar tool, for example when a user leaves the mouse cursor over an image, provides a small message describing the area. Additionally, in order to reduce right/left errors when associating images to an ROI, the imaging gallery does not allow right ROI to be associated to left breast abnormality, and a left ROI is not allowed to be associated with a right breast image or abnormality.

As depicted, a user can delete 922 the image clipping 910, or open the image clipping 910 in an individual ROI viewer upon the selection of magnification button 928.

FIG. 17 depicts an example embodiment of a ROI viewer 950 depicting an individual image 952. The ROI viewer 950 provides additional image manipulation tools, including an "invert" selector 954 that replaces the black pixels for white and the white pixels for black. The ROI viewer 950 also provides a "3D" button 956 that can support the activation of a separate 3D-modeling software package, one example of which is available from Clario, that enables the radiologist to view and rotate a composite three-dimensional image of the associated ROI. The radiologist may return to the ROI Gallery 900 by selecting either the "Exit" button 958 or the "Close Window" icon 960.

FIG. 18 is an example of a patient work-list form 1000 for use with embodiments of this invention. The work-list form 1000 allows the system to coordinate the retrieval of any high-resolution images in order to effectively utilize network bandwidth and system storage capacity. FIG. 19 is an example of a prior examinations form 1100 for use with embodiments of this invention. The prior examination form 1100 provides a radiologist with convenient access to a patient's prior medical image for review or comparison with a more current set of images.

An example embodiment of a diagnostic system can provide a user, or image interpreter, with a simultaneous view of a region of interest (ROI) in an image along with options for the user to include or discard the ROI through an automated sequence, select or confirm suggested attributes and features describing any abnormalities in the ROI, and to generate a report detailing the content of the image. Attributes and features describing any abnormalities in the ROI can be generated by performing a feature extraction process on an image, are displayed for user review as hints or suggestions. An exemplary hint can include an attribute designated from a plurality of possible attributes by highlighting the attribute with a different color, font, or format, than any non-highlighted attribute. The hints, or attribute suggestions, can indicate one or more of a variety of possible attribute descriptions that describe a specific feature of the ROI in the image. The automatic highlighting or hinting by the diagnostic system can aid a user, typically a radiologist, in quickly assessing the region of interest and selecting an appropriate description attributes for the ROI. The user can accept, modify, or reject any of the suggested attributes. Once the user is satisfied with the selected descriptions, incorporating either the suggested attributes or any user-selected description attributes, a report detailing the one or more regions of interest in the image can be automatically generated.

Attribute descriptions can include, for example, the location, attributes, and size of an abnormality within the region. The system can provide a user with the ability to select one or more highlighted hints, or select other descriptive attributes to be included in report. All hints can be selected by a common action (e.g., a "select all" option button or an appropriate voice command). All hints can alternatively be discarded or suppressed by a common action (e.g., a "deselect all" option button or an appropriate voice command).

In one embodiment, an automated diagnostic reporting system can be controlled by a voice recognition module, to select or deselect features and discard or include selected regions, without interacting with a keyboard or a pointing device (e.g., a mouse). A word library of voice commands can be limited to specific ROI or abnormality related terms to increase accuracy of recognition. Additionally, the system can have internal libraries to facilitate other keywords, slang or abbreviations that are user selected or germane to a particular image being analyzed. The entry of commands can be confirmed with or without computer voice feedback.

In one embodiment, the system can record both the features indicated by imaging processing software module as well as the interpretations of each image selected by a human user. The combination of the image processing software selections and the user selections can be packaged together for further statistical processing or analysis. The packaged software and user originated selection package can optionally include the image or ROI selected from the image.

In one embodiment, an automated diagnostic reporting system can perform an automatic import process that displays a ROI abnormality simultaneously along with the features extracted for that abnormality. In addition to the automatic processing mode a mechanism is provided to allow a radiologist to manually iterate through each of the regions or attributes as the data is imported from an automated diagnostic analysis. If a user selects the manual mode of operation a spreadsheet can provide a brief description for each region of interest.

FIG. 20 illustrates an example embodiment of a medical diagnostic reporting system that includes an abnormality-summary window or examination screen 1200. A user is presented examination screen 1200 after the selection of an exam. The automatic sequencing of the ROI can be initialized by the user selection of an "Auto-Next" feature 1202, by manually selecting a ROI on spreadsheet list 1204 containing text descriptors, or by selecting a ROI icon 1206 superimposed on graphical illustration 1208 reflecting the general position of the ROI on the patient. Upon selection of any of these methods the user can be presented with a detail screen 1300 displaying various descriptors describing the ROI in more detail, such as the example as depicted in FIG. 21.

In one embodiment the diagnostic reporting system can automatically extract the data pertaining to the image and a ROI in the image, and display the location on the title bar 1302 of screen 1300, and on the graphical diagram, as well as the suggestive feature set. A diagnostic reporting system can provide for the selection of keywords to build complete sentences for a report based on items extracted from the imaging data file and/or from items selected from the detail screen to describe features.

Figure 21:
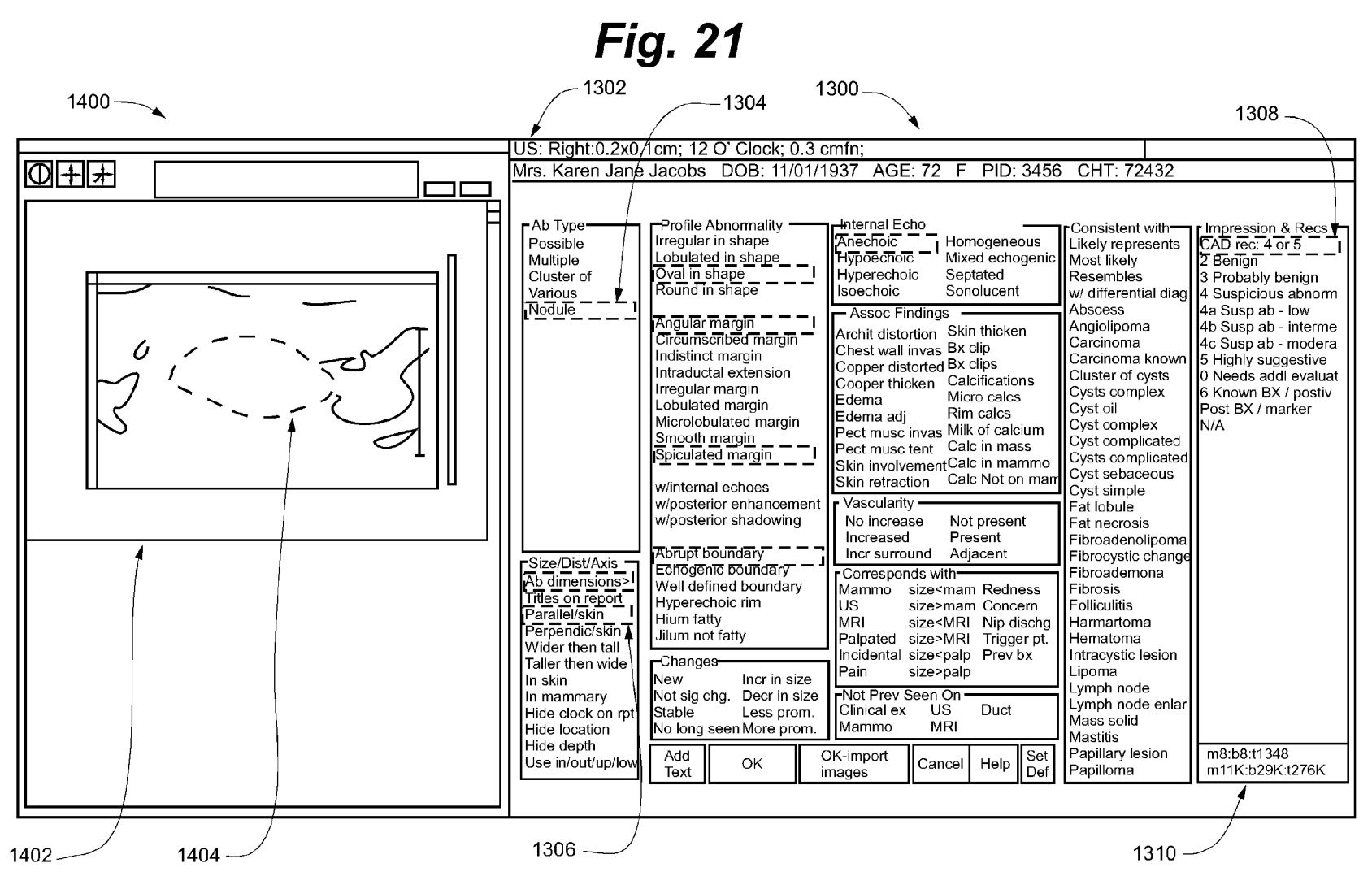

As depicted in FIG. 21, highlighted items 1306, which can be shown in a dashed box or alternatively displayed with a highlighted color (or other font or format), are imported from the data file associated with the image, processed, and are presented to the user as a suggestion or hint, or alternatively, presented as a selected item 1304, based on the users preferences. The user can select individual items (1304, 1306, 1308) to be included in a report by clicking or tapping on the item with a mouse or other pointing device, or by a voice activation command. Individual selections can be toggled on or off, to be included or excluded for a report, by clicking/tapping on the selection or repeating a voice command associated with the selection. The item is highlighted, or otherwise indicated by colored boarder or formatting, upon voice confirmation or the final generation of a report. The imaging viewing screen 1400 can include one or more images 1402 associated with the ROI abnormality 1404.

In one embodiment, individual items (1304, 1306, 1308) can be highlighted in a first color, for example yellow, to indicate a suggested ROI or image attribute as determined by an imaging processing software module or CAD tool. A second color, for example blue, can indicate that a user has selected or confirmed individual items. In this manner the diagnostic reporting system can indicate to the use which attributes are automatically generated by the system and which attributes were user selected.

In one embodiment, as allowed by some medical regulatory agencies, some or all of the attribute descriptions as generated by a software module or CAD tool can be presented to the user in the second color, indicating that no user modification or confirmation of the selection is necessary. The user can still change the attribute description regardless of the system suggestion. For example, if a CAD tool is approved by an appropriate medical regulatory agency to present the size and orientation of an abnormality depicted in a ROI the size and orientation of an abnormality can be presented in the second color, while all other CAD tool generated hints or suggestions are highlighted in the first color.

In one embodiment the system can suggest more than one abnormality description and require the user to select one of the two possible attributes, or an alternate third-attribute, before a report is generated. For example, item 1308 indicates that the CAD tool has hinted that abnormality 1404 should likely be categorized as either "4 Suspicious" or "5 Highly Suggestive." Before a report can be generated the user must select one of the attributes related to item 1308, indicating whether the user believes that abnormality 1404 is benign, probably benign, suspicious, highly suggestive, needs additional evaluation, or an alternate attribute known to those skilled in the art. In one embodiment multiple abnormality descriptions can be highlighted in the first color, prompting the user to select one of the presented abnormality descriptions. The user selected abnormality description will then be highlighted by the system in the second color.

In one embodiment a user can attach one or more images associated with a ROI in the report automatically by using the "OK-import" action. Only images indicated by highlighted border, which can be a default or user selectable setting, will be attached to the report. Images can be excluded by tapping on the image to deselect it, such as in the case of when multiple images of various planes are captured and may not be relevant to the report. The user can select "OK" to complete the description of ROI and then move to next ROI. If the user decides to not include a ROI in report user can select the "cancel" option. The user can use the profiler statistics window 1310, located in the lower right hand side of screen 1300 in FIG. 21, as a guide to compare the attributes of the displayed ROI with other, previously analyzed abnormalities with matching descriptors for reference on the probability of malignancy. The information displayed in profiler statistics window 1310 can include information from local or national databases of previously analyzed abnormalities, and present an indication of the number of cases with similar attributes that have previously been diagnosed as malignant or benign.

In one embodiment of the system, the user is presented with an image 1500 comprising patient tissue 1502 with a potential abnormality 1504. The user can select an area of a ROI by marking, or indicating with a bounding box 1508, a portion of the image area to be analyzed. The system can apply different analyzing software to scale and process the image 1500, and output an analysis that includes the boundaries and other attributes of the abnormality 1504.

As depicted in FIG. 22 a user can mark a relatively small seed-area 1508 within the boundary of an abnormality 1504. The analyzer, such as a CAD tool, uses the seed-area mark 1508 within the abnormality as a starting point to then locate the boundaries of the abnormality 1504. The image gallery image can then depict an automatic boundary outline depicting the complete abnormality 1504 by using one type of a CAD by placement of a "seed." The automatic boundary outline of the abnormality is determined by expanding the selected "seed" area until it surrounds the entirety of the abnormality 1504.

Alternatively, as depicted in FIG. 23, a user can draw a bounding box 1510 with an area greater then a generally small seed-area 1508 mark, potentially encompassing the all or the majority of a visible abnormality 1504. The CAD tool can then utilize an alternative analyzing code to determine the boundary the ROI by shrinking the selected boundary outline of the bounding box 1510. The resulting image with the selected ROI can be output to a gallery as outlined by bounding box 1510 or a larger area containing the complete abnormality area if the abnormality extends outside the selected bounding box area.

As shown by the preceding examples, the invention provides an integrated system and methods for the categorization, storage, retrieval, and correlation of a wide variety of patient data, diagnostic images from multiple imaging sources, test results, statistics and correspondence. The integration of a ROI profiler, a statistical analysis tool, and the gallery of clipped images, together with native high-resolution medical images provides radiologists and other medical professionals with a customizable tool that provides greater efficiencies while also improving the accuracy of patient diagnostic screenings.

The foregoing descriptions present numerous specific details that provide a thorough understanding of various embodiments of the invention. It will be apparent to one skilled in the art that various embodiments, having been disclosed herein, may be practiced without some or all of these specific details. In other instances, known components have not been described in detail in order to avoid unnecessarily obscuring the present invention. It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention. Accordingly, this application is intended to cover any adaptations or variations of the invention. It is manifestly intended that this invention be limited only by the following claims and equivalents thereof.

For purposes of interpreting the claims for the present invention, it is expressly intended that the provisions of Section 112, sixth paragraph of 35 U.S.C. are not to be invoked with respect to a given claim unless the specific terms "means for" or "step for" are recited in that claim.

Any incorporation by reference of documents above is limited such that no subject matter is incorporated that is contrary to the explicit disclosure herein. Any incorporation by reference of non-priority documents above is further limited such that no claims included in the documents are incorporated by reference herein and any definitions provided in the documents are not incorporated by reference herein unless expressly included herein.

The invention claimed is:

1. A configurable mammography diagnostic system, comprising:
   a plurality of electronic displays, at least one of the plurality of electronic displays configured to display a breast tissue image;
   a graphical user interface presented on at least one of the plurality of electronic displays and including:
      a breast tissue image on which at least one region of interest in the breast tissue image can be indicated,
      a plurality of possible characteristics from a predetermined medical lexicon according to which an automated categorization of a region of interest in the breast tissue image can be indicated, wherein each of the plurality of possible characteristics in the predetermined medical lexicon is associated with a unique alphanumeric value, and
      a profiler display configured to present statistical information related to a comparison of the automated categorization with a database of existing categorizations of a plurality of existing breast tissue images, each of the plurality of existing breast tissue images having been diagnosed;
   and
   a processing engine including a computer aided diagnosis (CAD) tool configured to identify the at least one region of interest in the breast tissue image, to provide the automated categorization of the region of interest, to present the automated categorization of the region of interest via the graphical user interface, and configured to dynamically update the profiler display based on a change in one or more of the plurality of possible characteristics and the unique alphanumeric value associated with the changed characteristic of the region of interest.

2. The system of claim 1, wherein the breast tissue image is selected from the group consisting of an X-ray image, a CT image, an MRI image, an ultrasound image, and a pathology image.

3. The system of claim 1, wherein each of the plurality of existing breast tissue images is cataloged in the database according to a characteristic of the breast tissue image.

4. The system of claim 1, wherein the plurality of possible characteristics from the predetermined medical lexicon includes an abnormality type, size, and profile.

5. The system of claim 1, wherein the computer aided diagnosis (CAD) tool is further configured to identify the plurality of possible characteristics from the predetermined medical lexicon of an abnormality depicted in the at least one region of interest.

6. The system of claim 1, wherein the computer aided diagnosis (CAD) tool is further configured to identify the at least one region of interest in the breast tissue image based on a user selection of a portion of the breast tissue image within the region of interest depicted in the breast tissue image.

7. The system of claim 1, wherein the computer aided diagnosis (CAD) tool is further configured to identify the at least one region of interest in the breast tissue image based on a user selection of a portion of the breast tissue image containing the region of interest depicted in the breast tissue image.

8. The system of claim 1, further comprising an interface to receive the change in one or more of the plurality of possible characteristics from the predetermined medical lexicon of the region of interest.

9. The system of claim 8, wherein the processing engine is operable to compare the automated categorization and the change in one or more of the plurality of possible characteristics from the predetermined medical lexicon of the region of interest.

10. system of claim 9, wherein an algorithm of the CAD tool is updated based on the comparison of the CAD automated categorization with the change in one or more of the plurality of possible characteristics from the predetermined medical lexicon.

11. The system of claim 8, wherein the processing engine is operable to compare the CAD automated categorization with pathological data related to a particular region of interest.

12. A method for managing patient mammography data comprising:
   obtaining a plurality of breast tissue images selected from the group consisting of an X-ray image, a CT image, an MRI image, an ultrasound image, and a pathology image;
   identifying a region of interest in at least one of the plurality of breast tissue images;
   obtaining, from a computer aided diagnosis (CAD) tool, a categorization of a breast tissue abnormality in the region of interest according to an established predetermined medical lexicon, the predetermined medical lexicon including a plurality of lexicon descriptors, wherein each of the plurality of lexicon descriptors in the predetermined medical lexicon is associated with a unique alphanumeric value;
   presenting the categorization of the breast tissue abnormality in the region of interest to a user;
   receiving a confirmation of the categorization from the user;
   associating the confirmed categorization with the region of interest;
   comparing the confirmed categorization of the region of interest with a database of existing categorizations of a plurality of existing breast tissue images, each of the plurality of existing breast tissue images having been diagnosed;
   presenting a profiler display comprising statistical information related to a comparison of the confirmed categorization with the database of existing categorizations; and
   dynamically updating the profiler display based on a modification in one or more of the plurality of lexicon descriptors and the unique alphanumeric value associated with the modified lexicon descriptor for the region of interest.

13. The method of claim 12, further comprising:
   receiving the modification of the categorization from the user.

14. The method of claim 12,
   wherein the profiler display comprises a diagnostic indicator comprising a number of instances of the categorization within the database of existing categorizations, a number of diagnoses of malignant abnormalities for the categorization among the existing categorizations, and a number of diagnoses of benign abnormalities for the categorization among the existing categorizations.

15. The method of claim 14, further comprising:
   updating the diagnostic indicator based on a comparison of the confirmed categorization and the existing categorizations.

16. The method of claim 15, further comprising:
   comparing the confirmed categorization with the computer aided diagnosis (CAD) categorization for the same region of interest.

17. The method of claim 12, wherein the database of existing categorizations includes an identified region of interest in each of a plurality of breast tissue images, and wherein each region of interest is associated with one of either a malignant or a benign diagnosis.

18. The method of claim 17, further comprising:
comparing the associated malignant or benign diagnosis of a region of interest in the database with a computer aided diagnosis (CAD) of the one of the plurality of breast tissue images associated with the region of interest.

19. A method for managing patient medical data comprising:
obtaining a plurality of tissue images selected from the group consisting of an X-ray image, a CT image, an MRI image, an ultrasound image, and a pathology image;
storing the plurality of tissue images in an image database having a non-volatile computer readable medium configured to retrievably store the plurality of tissue images;
performing a digital image analysis of the plurality of tissue images;
indentifying a region of interest in at least one of the tissue images;
performing a categorization of a tissue abnormality in the region of interest according to an established predetermined medical lexicon with a computer aided diagnosis (CAD) tool, the predetermined medical lexicon including a plurality of lexicon descriptors, wherein each of the plurality of lexicon descriptors in the predetermined medical lexicon is associated with a unique alphanumeric value;
presenting the categorization of the tissue abnormality in the region of interest to a user;
presenting the user with statistical information regarding the categorization;
comparing the categorization with a database including a plurality of diagnosed tissue abnormality categorizations; and
dynamically updating the statistical information based on a modification in one or more of the plurality of lexicon descriptors and the unique alphanumeric value associated with the modified lexicon descriptor for the region of interest.

20. The method of claim 19, further comprising:
receiving the modification of the categorization from the user.

21. The method of claim 19, wherein the identification of a region of interest in at least one of the tissue images includes a user selection of a portion of one of the tissue images within the region of interest depicted in the one of the tissue images.

22. The method of claim 19, wherein the identification of a region of interest in at least one of the tissue images includes a user selection of a portion of one of the tissue images containing the region of interest depicted in the one of the tissue images.

23. The method of claim 19, wherein the identification of a region of interest in at least one of the tissue images includes identifying a region of interest in at least one of the tissue images based on the digital image analysis.

\* \* \* \* \*